(12) United States Patent
Yamano

(10) Patent No.: US 7,874,212 B2
(45) Date of Patent: Jan. 25, 2011

(54) ULTRASONIC PROBE, ULTRASONIC FLAW DETECTION METHOD, AND ULTRASONIC FLAW DETECTION APPARATUS

(75) Inventor: Masaki Yamano, Suita (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 117 days.

(21) Appl. No.: 12/285,252

(22) Filed: Oct. 1, 2008

(65) Prior Publication Data
US 2009/0095087 A1      Apr. 16, 2009

Related U.S. Application Data

(63) Continuation of application No. PCT/JP2006/307221, filed on Apr. 5, 2006.

(51) Int. Cl.
  *G01N 29/26* (2006.01)
(52) U.S. Cl. .............................. 73/622; 73/593; 73/627; 73/640
(58) Field of Classification Search .................. 73/622, 73/593, 624–629, 632, 633, 637–639, 640
  See application file for complete search history.

(56) References Cited

U.S. PATENT DOCUMENTS

| | | | | |
|---|---|---|---|---|
| 3,610,028 A | * | 10/1971 | Sasaki | 73/628 |
| 4,605,009 A | * | 8/1986 | Pourcelot et al. | 600/109 |
| 4,686,408 A | * | 8/1987 | Ishiyama | 310/334 |
| 4,869,768 A | * | 9/1989 | Zola | 156/245 |
| 5,056,368 A | * | 10/1991 | Kawasaki et al. | 73/642 |
| 5,398,551 A | * | 3/1995 | Kawasaki et al. | 73/593 |
| 5,434,830 A | * | 7/1995 | Martin | 367/140 |
| 5,549,004 A | * | 8/1996 | Nugent | 73/622 |
| 5,686,668 A | * | 11/1997 | McLean | 73/622 |
| 5,814,731 A | * | 9/1998 | Alexander et al. | 73/644 |
| 5,969,255 A | * | 10/1999 | McLean | 73/622 |
| 6,813,950 B2 | * | 11/2004 | Glascock et al. | 73/633 |

(Continued)

FOREIGN PATENT DOCUMENTS

GB     2212919 A   *   9/1989

(Continued)

OTHER PUBLICATIONS

"Ultrasonic Flaw Detection", Japan Society for the Promotion of Science, 19th Steelmaking Committee, published by Nikkan Kogyo Shimbun, Ltd., pp. 224-227.

*Primary Examiner*—Jacques M Saint Surin
(74) *Attorney, Agent, or Firm*—Clark & Brody

(57) ABSTRACT

An ultrasonic probe performs flaw detection of a high (t/D) metal pipe. The front end portion of a transducer has at least a portion with an asymmetrically curved shape having a radius of curvature which progressively increases from one end towards the other end of the front end portion. The probe is disposed with respect to the pipe with its end having the smaller radius of curvature positioned on the side away from the direction of propagation of refracted waves, the end having a larger radius of curvature thereof positioned on the side in the direction of propagation of refracted waves. Angle beam flaw detection is carried out such that incident waves are generated which generate refracted longitudinal waves which do not reach the inner surface of the metal pipe and refracted transverse waves which are focused on the inner surface of the pipe.

10 Claims, 14 Drawing Sheets

U.S. PATENT DOCUMENTS

2009/0199642 A1 * 8/2009 Fukutomi et al. ............. 73/598

FOREIGN PATENT DOCUMENTS

| | | |
|---|---|---|
| JP | 1-43906 | 9/1989 |
| JP | 1-232256 | 9/1989 |
| JP | 4-142456 | 5/1992 |
| JP | 6-337263 | 12/1994 |
| JP | 10-90239 | 4/1998 |
| JP | 2003-90828 | 3/2003 |
| JP | 2004-251658 | 9/2004 |
| JP | 2006-105892 | 4/2006 |

* cited by examiner (a)

(b)

|  | Propagation of refracted transverse waves | Propagation of refracted longitudinal waves |
|---|---|---|
| Ratio (t/D) ≥ ca. 15% | (a) 7, 3, 6c, 6b, 6, 6a | (b) 7, 7a, 1, 7b, 2, 6c, 6, 6b, 6a |
| Ratio (t/D) < ca. 15% | (c) 7, 1, 3, 5, 5c, 5a, 5b | (d) Not exits in the metal Pipe |

Fig. 14

ULTRASONIC PROBE, ULTRASONIC FLAW DETECTION METHOD, AND ULTRASONIC FLAW DETECTION APPARATUS

CROSS REFERENCE TO RELATED APPLICATION

This application is a continuation of International Patent Application No. PCT/JP2006/307221, filed Apr. 5, 2006. This PCT application was not in English as published under PCT Article 21(2).

TECHNICAL FIELD

This invention relates to an ultrasonic probe, an ultrasonic flaw detection method, and an ultrasonic flaw detection apparatus. Specifically, the present invention relates to an ultrasonic probe, an ultrasonic flaw detection method, and an ultrasonic flaw detection apparatus which can detect minute flaws present in the outer surface, the inner surface, the interior and the like of a tubular metal body being inspected and particularly a metal pipe for which the ratio (t/D) of the wall thickness t with respect to the outer diameter D is at least 15%, for example, with certainty and with high precision by angle beam flaw detection.

BACKGROUND ART

A known nondestructive testing method for detecting flaws which are present in a tubular metal body being inspected, for example a metal pipe which is used as an oil country tubular good (oil well tubing and casing), line pipe, or a mechanical part (such as a hollow shaft, mechanical tubing used in an automotive part, or a stainless steel pipe used in high temperature environments) without destroying it is the ultrasonic flaw detection method in which ultrasonic waves are impinged on a metal pipe and the reflected echoes from flaws present in its interior are detected. Among ultrasonic flaw detection methods, the angle beam ultrasonic flaw detection method in which ultrasonic waves are impinged on a surface undergoing flaw detection at an angle is used in order to detect flaws in the inner surface, in the outer surface, in the interior, and in welds of a metal pipe. As is well known, in the angle beam flaw detection method, normally, an angle probe is used which has an housing in which a transducer disposed so as to transmit ultrasonic waves at an angle with respect to a surface undergoing flaw detection, a sound absorbing material, and a couplant for contacting the surface undergoing flaw detection (a wedge or the like made of an acrylic or other resin) are included. In cases in which water is used as a couplant, instead of a wedge or other couplant being housed in a casing, flaw detection is carried out with the metal pipe and the angle probe immersed in water.

FIG. 11 is an explanatory view showing the relationship between incident waves 1 and refracted waves 2 and 3 in an angle beam flaw detection method. The dashed line in FIG. 11 and in FIGS. 12 and 13 to be described later indicates a normal to the flaw detection plane O.

As shown in FIG. 11, in the angle beam flaw detection method, when incident ultrasonic waves 1 are obliquely incident on the flaw detection surface O of a metal pipe (medium II), even in the case where the incident ultrasonic waves 1 emitted at an unillustrated transducer are longitudinal ultrasonic waves, refracted waves in the form of refracted longitudinal waves 2 and refracted transverse waves 3 are propagated inside the metal pipe. If the sound velocity of incident ultrasonic waves 1 in medium I (generally a liquid couplant typified by water or a wedge housed inside an angle probe) is Vi, the sound velocity of refracted transverse ultrasonic waves 3 in medium II (a metal pipe which is a tubular body being inspected) is Vs, the sound velocity of refracted longitudinal ultrasonic waves 2 in medium II is VL, the angle of incidence of incident waves 1 is θi, the angle of refraction of refracted transverse waves 3 is θs, and the angle of refraction of refracted longitudinal waves 2 is θL, then Snell's law, i.e., the relationship $\sin(\theta i/Vi) = \sin(\theta s/Vs) = \sin(\theta L/VL)$ is established between the incident waves 1 and the refracted waves 2 and 3.

FIG. 12 is an explanatory view showing the propagation of refracted waves 2 and 3 in the interior 5c of a metal pipe 5. As shown in this figure, if incident waves 1 from a transducer 4 of an ultrasonic probe are incident on the metal pipe 5 with an angle of incidence θi, refracted ultrasonic waves 2 and 3 are propagated in the interior 5c of the metal pipe 5 while repeatedly reflecting off the inner surface 5a and the outer surface 5b of the metal pipe 5. If a flaw is present on the inner surface 5a or the outer surface 5b or in the interior 5c of the metal pipe 5, a reflected echo of ultrasonic waves reflected from the flaw returns to the transducer 4 and is received as a flaw echo. In this manner, ultrasonic flaw detection of the metal pipe 5 is carried out.

As explained with respect to FIG. 11, refracted longitudinal waves 2 and refracted transverse waves 3 are both propagated in the interior 5c of the metal pipe 5, namely, in medium II, so it is difficult to distinguish whether an echo received by the transducer 4 is due to refracted longitudinal waves 2 or refracted transverse waves 3.

As a result, the location of a flaw cannot be specified, the wave shape of a received signal becomes complicated, and the S/N ratio of a flaw echo decreases.

Consequently, in general, in order to carry out ultrasonic flaw detection of a steel pipe 5 by the angle beam flaw detection method, the angle of incidence θi is set at an angle which is larger than the critical angle of the refracted longitudinal waves 2 so that refracted transverse waves 2 are not included in the refracted waves propagated in the interior 5c of the metal pipe 5. For example, when medium I is water, the sound velocity Vi of refracted longitudinal waves 2 in medium I at room temperature is approximately 1500 meters per second, and if the sound velocity VL of refracted longitudinal waves 2 in the metal pipe 5 which is medium II is 5900 meters per second and the sound velocity Vs of refracted transverse waves 3 is 3200 meters per second, then from Equation 1, the angle of incidence θi which becomes the critical angle of the refracted longitudinal waves 2 (θL=90°) becomes approximately 15°, and the angle of refraction θs of refracted transverse waves 3 becomes approximately 33°. Therefore, in principle, if the angle of incidence of θi of incident waves 1 is set to be at least 15°, only refracted transverse waves 3 are present in medium II.

In recent years, there has been an increasing demand not only for a reduction in weight but also an increase in strength of a steel pipe used as an oil country tubular good, line pipe, mechanical part, or the like. As a result, there is an increasing demand for a metal pipe having a large ratio (t/D) of the wall thickness t to the outer diameter D which is as high as at least 15%, for example (referred to in this specification as "high t/D metal pipes"). However, as shown in FIG. 13 which is an explanatory view of the situation when carrying out flaw detection on a high t/D metal pipe 6 by the angle beam flaw detection method, when angle beam flaw detection of a high t/D metal pipe 6 is carried out by the above-described conventional ultrasonic flaw detection method, even in case where waves are incident from the outer surface 6 of a high t/D metal pipe 6 with an angle of incidence θi of at least the critical angle of longitudinal ultrasonic waves of the ultrasonic waves 1, the refracted transverse waves 3 which are propagated in the interior 6c of the metal pipe 6 sometimes follow a propagation path to the outer surface 6b without reaching the inner surface 6a of the metal pipe 6. In this case, flaws present in the vicinity of the inner surface 6a of the metal pipe 6 cannot be detected.

Patent Document 1, for example, discloses using a first ultrasonic probe having a first transducer for which the refraction angle θs of refracted transverse waves inside a metal pipe is increased, such as to greater than 35°, and a second transducer for which the refraction angle θs is decreased, such as to less than 35°. The first transducer is used by itself when performing flaw detection of a metal pipe 5 having a usual ratio (t/D), and the first transducer and the second transducer are used together when performing flaw detection of a high t/D metal pipe 6.

If the ultrasonic probe disclosed in Patent Document 1 is used to perform flaw detection of a high t/D metal pipe 6, it is in fact possible for refracted transverse waves generated by the second transducer to reach the inner surface of the high t/D metal pipe 6. However, when the second transducer is used, not only refracted transverse waves but also refracted longitudinal waves are generated, so the position of a flaw can not be specified, the waveform of the received signal becomes complicated, or the S/N ratio of flaw echoes decreases.

Non-patent Document 1, for example, discloses an invention in which an acoustic lens having a front end surface with a spherical or cylindrical shape is disposed in front of a transducer, or in which the front end surface of the transducer is formed into a spherical or cylindrical shape, and when detecting flaws which are short in the axial direction of a metal pipe and have a small depth, an acoustic lens having a spherical end surface or a probe formed to have a spherical end surface is used, and when detecting flaws which are shallow but continuous in the pipe axial direction, an acoustic lens having a cylindrical end surface or a transducer which is formed to have a cylindrical end surface with the direction of curvature of the cylindrical surface extending in the circumferential direction of the metal pipe is used, whereby ultrasonic waves incident on the metal pipes are focused onto the metal pipe, and as a result, the strength of echoes is increased, whereby detection can be performed with a good S/N ratio and minute flaws formed in the interior of a metal pipe can be detected with high accuracy.

FIG. 14 is an explanatory view showing the propagation of refracted longitudinal waves 2 and refracted transverse waves 3 which are propagated in the interior of metal pipes 5 and 6 when refracted transverse waves 3 are focused on the inner surface of the metal pipes 5 and 6 in accordance with the invention disclosed in Non-patent Document 1. FIG. 14(*a*) shows refracted transverse waves 3 when using a high t/D metal pipe 6 for which the ratio (t/D) is at least approximately 15%, FIG. 14(*b*) shows refracted longitudinal waves 2 when using this high t/D metal pipe 6, FIG. 14(*c*) shows refracted transverse waves 3 when using a metal pipe 5 for which the ratio (t/D) is less than approximately 15% (around 10%), and FIG. 14(*d*) shows the case when using this metal pipe 5.

As shown in FIG. 14(*c*) and FIG. 14(*d*), in the case of a usual metal pipe 5 for which the ratio (t/D) is less than approximately 15%, ultrasonic flaw detection can be carried out by easily establishing conditions such that refracted transverse waves 3 are focused on the inner surface 5a of the metal pipe 5 and refracted longitudinal waves 2 are not generated. In contrast, as shown in FIG. 14(*a*) and FIG. 14(*b*), in the case of a high t/D metal pipe 6 for which the ratio (t/D) is at least approximately 15%, if it is attempted to make refracted transverse waves 3 reach the inner surface 6a of the metal pipe 6, refracted longitudinal waves 2 are also produced.

A portion of the refracted longitudinal waves 2 which are generated reach the inner surface 6a of the metal pipe 6 in the same manner as the refracted transverse waves 3, and the arriving refracted longitudinal waves 2 are propagated at an angle which is close to perpendicular with respect to the inner surface 6a of the metal pipe 6. As a result, they are reflected multiple times between the inner surface 6a and the outer surface 6b of the metal pipe 6.

FIG. 15 is a graph showing one example of reflected echoes observed when performing flaw detection of a high t/D metal pipe 6 in this manner. As illustrated by the graph in FIG. 15, an echo from an inner surface flaw by refracted transverse waves 3 is buried among the multiply reflected echo of the refracted longitudinal waves 2. This multiply reflected echo of the refracted longitudinal waves 2 becomes a noise signal which interferes with detection of flaws, and minute flaws cannot be detected with a high S/N ratio. Depending on the wall thickness of the metal pipe 6, a flaw echo is completely buried in the flood of multiply reflected echoes of the refracted longitudinal waves 2, and even an experienced inspector cannot distinguish flaw echoes.

Patent Document 2 discloses an invention in which flaw echoes in a high t/D metal pipe are found by alternatingly performing flaw detection at two frequencies in which flaw echoes and multiply reflected echoes are detected by flaw detection at a certain frequency and only multiply reflected echoes are detected by flaw detection at a different frequency, and the multiply reflected echoes which are noise are removed by differential processing of the flaw detection waveforms at these frequencies.

Patent Document 1: JP 10-90239 A1 (1998)
Patent Document 2: JP 06-337263 A1 (1994)
Non-patent Document 1: "Ultrasonic Flaw Detection", Japan Society for the Promotion of Science, 19th Steelmaking Committee, published by Nikkan Kogyo Shimbun, Ltd., pp. 224-227.

DISCLOSURE OF THE INVENTION

Problem Which the Invention is to Solve

However, the invention disclosed in Patent Document 2 has the problems (a)-(c) listed below.

(a) It is necessary to alternatingly collect flaw detection waveforms at two different frequencies at roughly the same location, so the detection efficiency is unavoidably reduced to roughly one half.

(b) When the strength of flaw echoes is the same or smaller than the strength of the adjoining multiply reflected echoes, or when the flaw echoes appear in a location extremely close to the multiply reflected echoes, even when differential processing of the multiply reflected echoes is carried out, the majority of the flaw echoes end up being subtracted, and flaw echoes cannot be detected based on the waveform after differential processing.

(c) It is necessary to use a special ultrasonic flaw detection apparatus which can perform flaw detection at multiple frequencies, so detection costs necessarily increase.

The present invention was made in order to solve these problems (a)-(c) of the prior art, and its object is to provide an ultrasonic probe, an ultrasonic flaw detection method, and an ultrasonic flaw detection apparatus which can perform flaw detection of minute flaws with high accuracy and with certainty by angle beam flaw detection, the minute flaws being present in the outer surface, the inner surface, the interior, or the like of a tubular metal body being inspected used as a oil country tubular good, line pipe, or mechanical part (hollow vehicle axle, mechanical tubing used in an automotive part and the like, a stainless steel pipe used in a high temperature environment, and the like) and particularly of a metal pipe having a ratio (t/D) of the wall thickness t to the outer diameter D of at least 15%.

Means for Solving the Problem

As a result of performing diligent investigations for solving the above-described problems, the present inventors obtained the information (A) and (B) described below and completed the present invention.

(A) As explained while referring to FIG. 14(a) and FIG. 14(b), if flaw detection is carried out while transmitting incident waves 1 from a transducer 7 having a front end surface which is spherical or cylindrical, i.e., for which the longitudinal cross-sectional shape of the front end portion is a circular arc and focusing refracted transverse waves 3 on the inner surface 6a of a high t/D metal pipe 6, simultaneously generated refracted longitudinal waves 2 reach the inner surface 6a of the metal pipe 6. The refracted longitudinal waves 2 which reach the inner surface 6a of the metal pipe 6 are formed by incident waves 1 which are transmitted from the portion 7a positioned on the side in the direction of propagation of ultrasonic waves as viewed from the center of the metal pipe 6 (the left side in the plane of FIG. 14) with a small angle of incidence on the outer surface 6b of the metal pipe 6.

(B) FIG. 1(a) is an explanatory view showing a comparison between the longitudinal cross-sectional shape of the front end portion 8c of an improved transducer 8 conceived by the present inventor and the longitudinal cross-sectional shape of the front end portion 7c of the above-described transducer 7. FIG. 1(b) is an explanatory view comparing the state during angle beam flaw detection of a high t/D metal pipe 6 (outer diameter of 40 mm, wall thickness of 10 mm) using this transducer 8 and during angle beam flaw detection of the high t/D metal pipe 6 using the transducer 7. In FIG. 1(a), the location marked 0 mm on the abscissa shows the center of the high t/D metal pipe 6 which is the object undergoing flaw detection.

By satisfying the following two conditions, i.e., (i) as shown in FIG. 1(a), the front end portion 8c of the transducer 8 constituting an angle probe is a shape at least a portion of which is an asymmetrically curved shape having a radius of curvature which progressively increases from one end 8b towards the other end 8a, and (ii) angle beam flaw detection is carried out while the transducer 8 is disposed in a predetermined position with respect to the high t/D metal pipe 6 so that, as viewed from the center of the metal pipe 6, one end 8b of the front end portion 8c of the transducer 8 is located on the side away from the direction of propagation of refracted waves in the metal pipe 6 (on the right side in FIG. 1(a)) and the other end 8a of the front end portion 8c of the transducer 8 is positioned on the side in the direction of propagation of refracted waves (on the left side in FIG. 1(a)), as shown by the solid line arrow in FIG. 1(b), large values for the angle of incidence of incident waves 1 transmitted from the other end 8a and for the angle of refraction of the refracted longitudinal waves 2 can be obtained. As a result, refracted longitudinal waves 2 directly reach the outer surface 6b of the metal pipe 6 without reaching the inner surface 6a of the metal pipe 6. Accordingly, the occurrence of multiply reflected echoes by the refracted longitudinal waves 2 can be eliminated.

As stated above, the longitudinal cross-sectional shape of the front end portion 8c of the transducer 8 is a shape in which at least a portion thereof has an asymmetrically curved shape having a radius of curvature which continuously increases from the one end 8b towards the other end 8a. The size and the degree of increase of the radius of curvature, the proportion of the portion having an asymmetrically curved shape, and other parameters can be suitably and separately selected taking into consideration the type of metal pipe 6 and the like so that refracted transverse waves 3 reach the inner surface 6a of the metal pipe 6 and are focused at a specific location in the vicinity of the inner surface 6a.

The present invention is an ultrasonic probe for flaw detection of a tubular metal body being inspected by obliquely impinging ultrasonic waves from a transducer housed therein on the tubular body being inspected and generating refracted longitudinal waves and refracted transverse waves which propagate inside the tubular body being inspected, characterized in that the front end portion of the transducer has at least a portion with an asymmetrically curved shape having a radius of curvature which progressively increases from one end towards the other end of the portion.

In addition, the present invention is an ultrasonic probe which has a transducer disposed therein and an acoustic lens which is disposed in front of the transducer in the direction of generation of ultrasonic waves, and which detects flaws in a tubular metal body being inspected by obliquely impinging ultrasonic waves on the tubular body being inspected and generating refracted longitudinal waves and refracted transverse waves which propagate inside the tubular body being inspected, characterized in that the front end portion of the acoustic lens has at least a portion having an asymmetrically curved shape having a radius of curvature which progressively increases from one end towards the other end of the portion.

The present invention is also an ultrasonic probe which detects flaws in a tubular metal body being inspected by obliquely impinging ultrasonic waves on the tubular body being inspected from a transducer housed therein and generating refracted longitudinal waves and refracted transverse waves which propagate inside the tubular body being inspected, characterized in that the transducer comprises a plurality of oscillation-generating elements disposed side by side, and interference between ultrasonic waves generated by the plurality of oscillation-generating elements causes to generate incident waves having a wave front in which at least a portion thereof has an asymmetrically curved shape with a radius of curvature which progressively increases from one end towards the other end of the portion.

In an embodiment, an ultrasonic probe according to the present invention is equipped with a delay time adjusting device which generates incident waves by adjusting the delay time for transmitting and receiving oscillating waves by the plurality of oscillation-generating elements. In this case, an acoustic lens is preferably provided in front of the transducer as viewed in the direction of ultrasonic wave transmission.

In these ultrasonic probes according to the present invention, an example is given in which the tubular body being inspected is a metal pipe for which the ratio of the wall thickness to the outer diameter is at least 15%.

From another aspect, the present invention is a method of ultrasonic flaw detection characterized in that angle beam flaw detection is carried out with one of the above-described ultrasonic probes according to the present invention which is disposed with respect to a metal tubular body being inspected such that, as viewed from the center of the tubular metal body, the end having a smaller radius of curvature of the front end portion of a transducer or an acoustic lens constituting the ultrasonic probe is positioned on the side away from the direction of propagation of refracted waves in the tubular body and the end having a larger radius of curvature thereof is positioned on the side in the direction of propagation of the refracted waves, and such that incident waves can be generated which generate refracted longitudinal waves which do not reach the inner surface of the tubular body being inspected and refracted transverse waves which are focused on the inner surface of the tubular body being inspected.

In addition, the present invention is a method of ultrasonic flaw detection characterized in that angle beam flaw detection is carried out with the above-described ultrasonic probe according to the present invention which is disposed with respect to a metal pipe such that, as viewed from the center of the tubular metal body being inspected, the end having a smaller radius of curvature of the wave front at the end of incident waves which are generated by a transducer constituting the ultrasonic probe is positioned on the side away from the direction of propagation of refracted waves in the metal pipe and the end of the wave front having a larger radius of curvature thereof is positioned on the side in the direction of propagation of refracted waves, and such that incident waves can be generated which generate refracted longitudinal waves which do not reach the inner surface of the metal pipe and refracted transverse waves which are focused on the inner surface of the metal pipe.

In addition, the present invention is an ultrasonic flaw detection method characterized by performing flaw detection of a tubular metal body being inspected for which the ratio of the wall thickness to the outer diameter is a value greater than 15% using the above-described ultrasonic flaw detection method according to the present invention.

From yet another standpoint, the present invention is an ultrasonic flaw detection apparatus characterized by being equipped with the above-described ultrasonic probe according to the present invention.

EFFECTS OF THE INVENTION

According to the present invention, by disposing an ultrasonic probe according to the present invention in a suitable location with respect to a tubular metal body being inspected, particularly even with a high t/D metal pipe for which the ratio (t/D) is at least 15%, among the refracted waves propagating inside the tubular body being inspected, refracted transverse waves can be focused on the inner surface of the tubular body being inspected, while refracted longitudinal waves can be prevented from reaching it. Therefore, the strength of reflected echoes from minute flaws is increased by focusing the refracted transverse waves, while the occurrence of multiply reflected echoes due to refracted longitudinal waves can be eliminated because the refracted longitudinal waves follow a path of propagation which does not reach the inner surface of the tubular body being inspected. As a result, high-accuracy angle beam flaw detection can be carried out with certainty, particularly on high t/D metal pipes.

In this manner, according to the present invention, flaw detection of minute flaws present inside a tubular body being inspected and particularly inside a high t/D metal pipe for which the ratio (t/D) is at least 15% can be carried out with high accuracy and with certainty by angle beam flaw detection without a decrease in detecting efficiency or an increase in detection costs.

BRIEF EXPLANATION OF THE DRAWINGS

FIG. 14 is an explanatory view showing the propagation of refracted longitudinal waves and refracted transverse waves which are propagated inside a metal pipe when refracted transverse waves are focused on the inner surface of a metal pipe in the invention disclosed in Non-patent Document 1, FIG. 14(a) showing refracted transverse waves when using a metal pipe for which the ratio (t/D) is at least approximately 15%, FIG. 14(b) showing refracted longitudinal waves when using this metal pipe, FIG. 14(c) showing refracted transverse waves when using a metal pipe for which the ratio (t/D) is less than approximately 15% (around 10%), and FIG. 14(d) show the case using this metal pipe.

Figure 1:
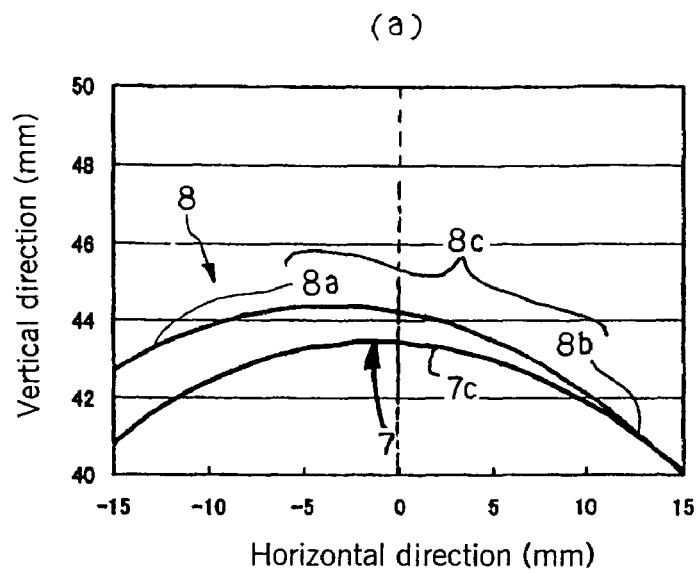
FIG. 1(a) is an explanatory view comparing the longitudinal cross-sectional shape of the front end portion of an improved transducer conceived by the present inventor to the longitudinal cross-sectional shape of the front end portion of a conventional transducer.
FIG. 1(b) is an explanatory view comparing the state of angle beam flaw detection of a high t/D metal pipe using this improved transducer and the state of angle beam flaw detection of a high (t/D) metal pipe using the conventional transducer.
Figure 1:
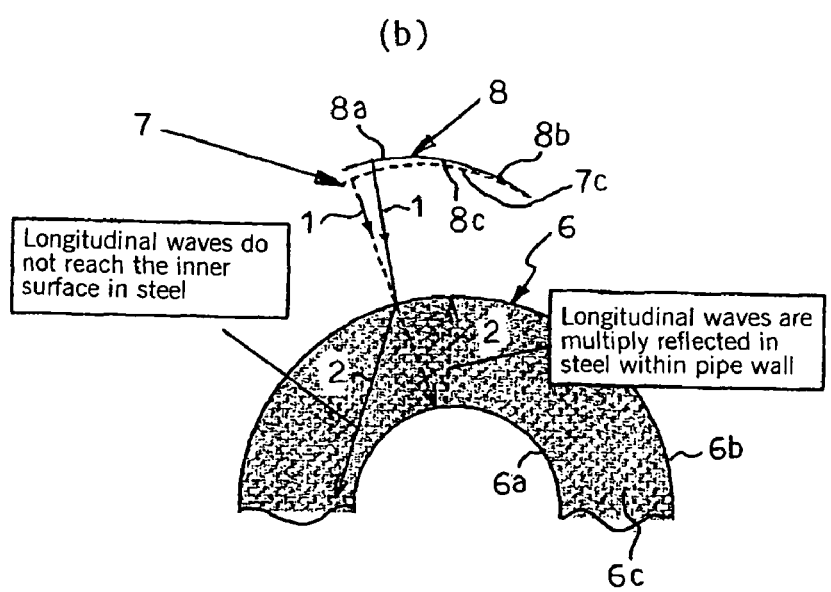

LIST OF REFERENTIAL NUMERALS 0 flaw detection surface
1 incident waves
2 refracted longitudinal waves
3 refracted transverse waves
4 transducer
5 metal pipe
5a inner surface
5b outer surface
5c interior
6 high t/D metal pipe
6a inner surface
6b outer surface
6c interior
7 transducer
9 metal pipe
10 ultrasonic flaw detection apparatus
11 ultrasonic probe
12 ultrasonic flaw detector
13 alarm
14 marking device
15 transducer
15a other end
15 one end
15c front end portion
16 high t/D metal pipe
16a inner surface
16b outer surface
16c interior
17 focal point
18 origin of propagation
19 pulser
20 preamplifier
22 main amplifier
23 flaw determining part
30 ultrasonic flaw detection apparatus
31 transducer
32 ultrasonic probe
33 probe holder
34 lower horizontal arm
35 vertically movable arm
36 horizontally movable arm
37 upper horizontal arm
38 pipe following mechanism
39 air cylinder
40 ultrasonic flaw detection apparatus
41 transducer
41a piezoelectric element
42 ultrasonic probe
43 transmitting circuit
43 receiving circuit
45 alarm
46 marking device
47 metal pipe
47a outer surface
48 pulser
49 delay circuit (transmission delay circuit)
50 preamplifier
51 delay circuit (reception delay circuit)
52 adder
53 main amplifier
54 flaw determining part Best Mode for Carrying Out the Invention First Embodiment Below, a best mode for carrying out an ultrasonic probe, an ultrasonic flaw detection method, and an ultrasonic flaw detection apparatus according to the present invention will be explained in detail while referring to the attached drawings. In the following explanation, an example will be given of the case in which a tubular metal body being inspected is a high t/D metal pipe 16 for which the ratio (t/D) of the wall thickness t to the outer diameter D is at least 15%.

Figure 2:
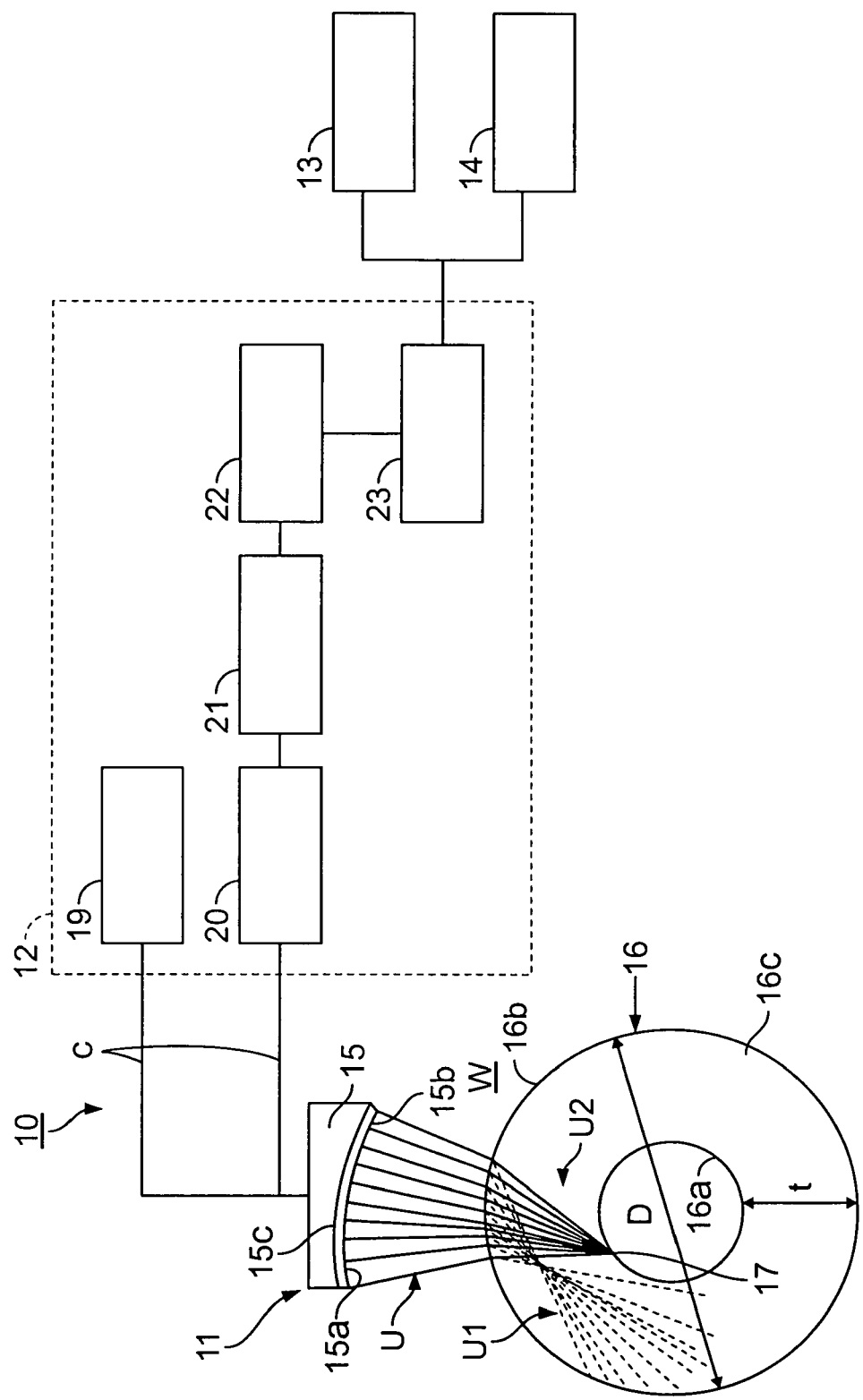
FIG. 2 is a block diagram schematically showing the structure of an embodiment of an ultrasonic flaw detection apparatus.

FIG. 2 is a block diagram schematically showing the structure of this embodiment of an ultrasonic flaw detection apparatus 10.

As shown in this figure, this embodiment of an ultrasonic flaw detection apparatus 10 has an ultrasonic probe 11, an ultrasonic flaw detector 12, an alarm 13, and a marking device 14. These will be explained in sequence.

[Ultrasonic Probe 11]

Like a conventional ultrasonic probe of this type, the ultrasonic probe 11 has a casing which houses a sound absorbing material, a transducer 15 which is installed so as to transmit ultrasonic waves obliquely with respect to a surface undergoing flaw detection, and the like. The casing, the sound absorbing material, and the like can be well-known conventional members, so illustration thereof in FIG. 2 and explanation thereof will be omitted. In this embodiment, water is used as a couplant, and a casing is used which can be filled with water so that the surface of a high t/D metal pipe 16 undergoing flaw detection is immersed in water.

In this embodiment, the transducer 15 is excited at prescribed periods by input of a transmission signal from a pulser 19 which constitutes a below-described ultrasonic flaw detector 12. As a result, incident ultrasonic waves U are impinged at an angle on the outer surface 16b of the high t/D metal pipe 16 through a couplant in the form of water W. The incident waves U are propagated in the interior 16c of the high t/D metal pipe 16 as refracted waves comprising refracted longitudinal waves U1 and refracted transverse waves U2. Reflected echoes (flaw echoes and the like) of refracted transverse waves U2 due to flaws and the like present on the outer surface 16b, on the inner surface 16a, or in the interior 16c of the high t/D metal pipe 16 are received by the transducer 15. This received signal is transmitted to the ultrasonic flaw detector 12. In this manner, angle beam flaw detection of the high t/D metal pipe 16 is carried out.

As explained above while referring to FIGS. 1(a) and 1(b), a portion of the front end 15c of this transducer 15 is formed so that it has a portion with an asymmetrically curved shape for which the radius of curvature progressively increases from one end 15b thereof towards the other end 15a thereof from a radius of curvature $\rho_1$ to a radius of curvature $\rho_2$. In order to accurately form the front end portion 15c so as to have this portion with an asymmetrically curved shape at least partially, the transducer 15 is constituted not by a commonly used ceramic piezoelectric element typified by PZT ($PbZrO_3$—$PbTiO_3$) which is hard and difficult to machine, but by a PZT-epoxy composite piezoelectric element, which has good machinability.

Figure 3:
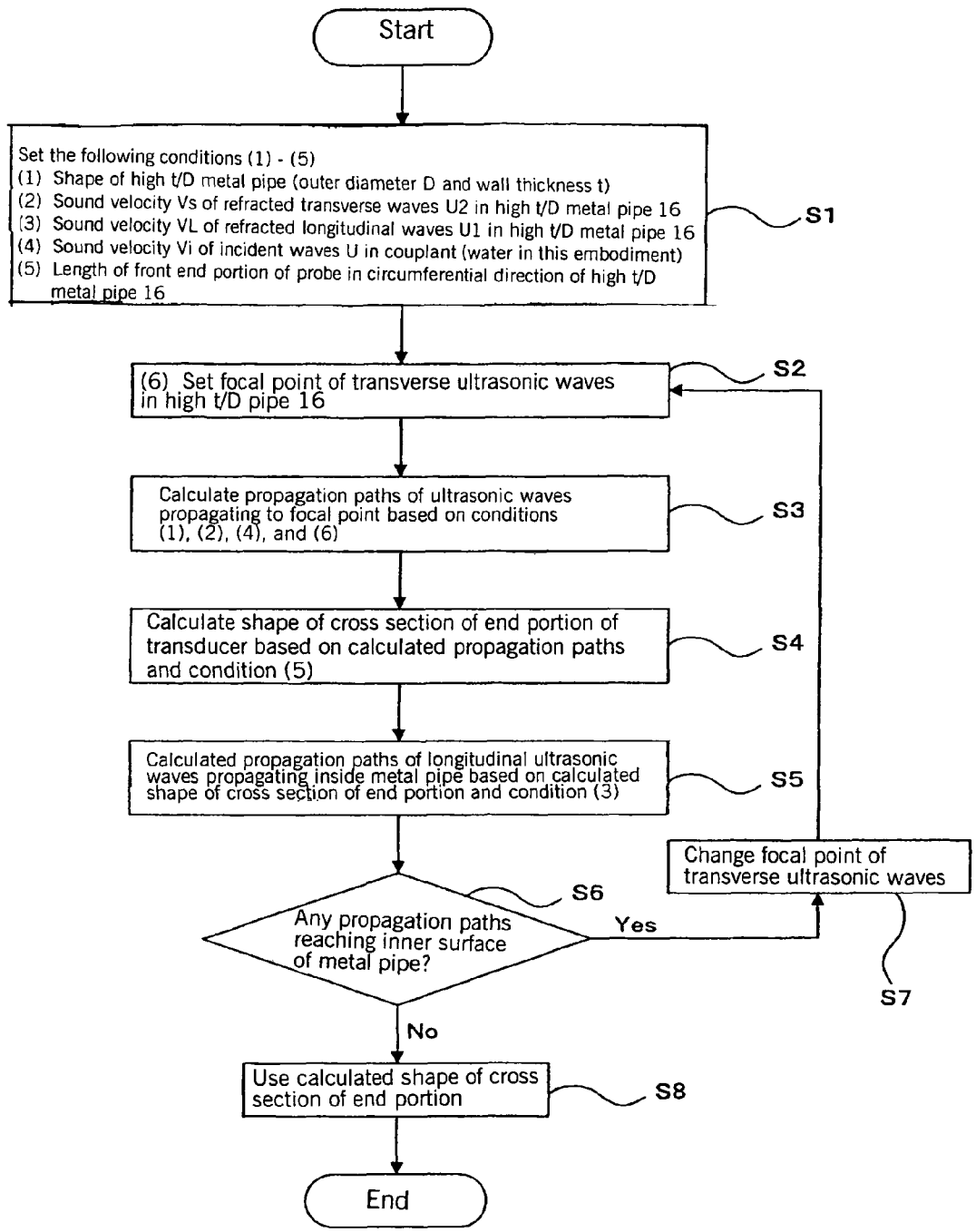
FIG. 3 is a block diagram schematically showing the steps in designing the shape of the front end portion of a transducer.

The portion of the front end 15c having an asymmetrically curved shape is determined based on the following steps (abbreviated below as S) S1-S8, for example, A procedure for determining the portion of the front end 15c having an asymmetrically curved shape will be explained. FIG. 3 is a flow diagram schematically showing the steps in designing the shape of the front end portion 15c of the transducer 15. FIGS. 4A-4D are explanatory views showing the steps in designing the shape of the front end portion 15c of the transducer 15 when a high t/D metal pipe 16 with an outer diameter of 40 mm and a wall thickness of 10 mm is being inspected.

As shown in FIG. 3, in S1, (1) the shape (the outer diameter D and the wall thickness t) of the high t/D metal pipe 16, (2) the sound velocity Vs of refracted transverse waves U2 in the high t/D metal pipe 16, (3) the sound velocity VL of refracted longitudinal waves U1 in the high t/D metal pipe 16, (4) the sound velocity Vi of incident waves U in the couplant (which is water in this embodiment), and (5) the length of the front end portion of the transducer 15 in the circumferential direction of the high t/D metal pipe 16 are set.

The sound velocity Vi of incident waves in the couplant, the sound velocity Vs of refracted transverse waves U2 in the high t/D metal pipe 16, and the sound velocity VL of refracted longitudinal waves U1 may use known numerical data based on the type of couplant and the material and the like of the high t/D metal pipe 16, or previously collected experimental data may be used as set values.

The length of the front end portion of the transducer 15 in the circumferential direction of the high t/D metal pipe 16 may be set to a length so as to obtain an adequate sensitivity in transmission and reception and so that actual manufacture is possible. Usually, although it depends upon the shape of the high t/D metal pipe 16 and the dimensions of the flaws to be detected as well as the material properties of the transducer and the like, the length of the transducer 15 in the circumferential direction of the high t/D metal pipe 16 is around 6-20 mm. Then, the procedure proceeds to S2.

Figure 4A:
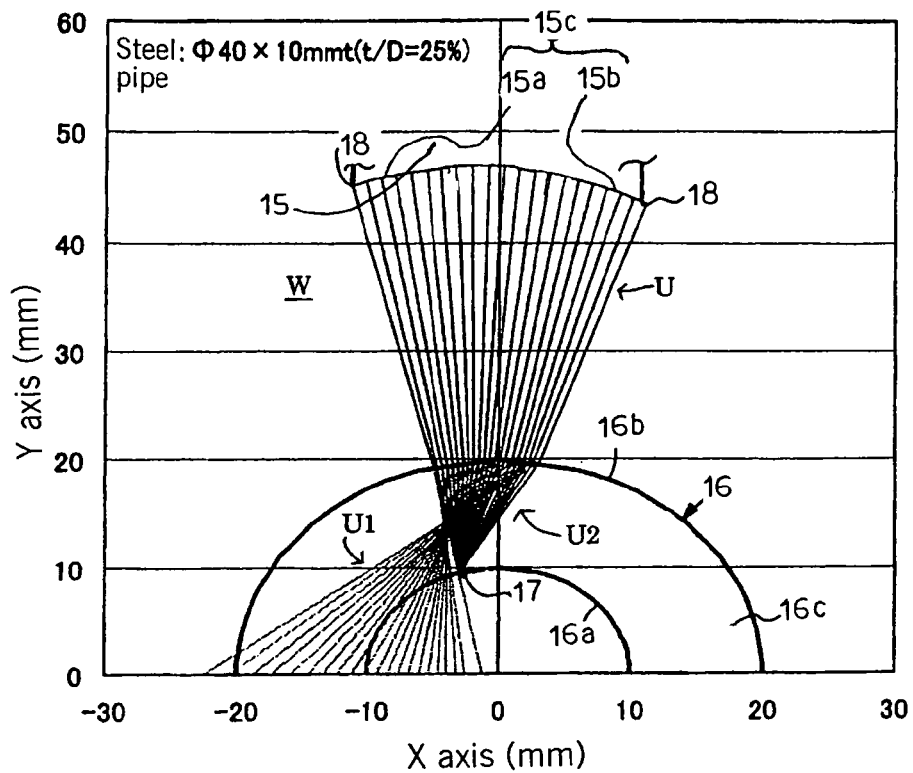
FIG. 4A is an explanatory view showing a step in designing the shape of the front end portion of a transducer when a high t/D metal pipe with an outer diameter of 40 mm and a wall thickness of 10 mm is the object being inspected.

In S2, as shown in FIG. 4A, (6) the focal point 17 of refracted transverse waves U2 on the inner surface 16a of the high t/D metal pipe 16 is suitably provisionally set.

Figure 6:
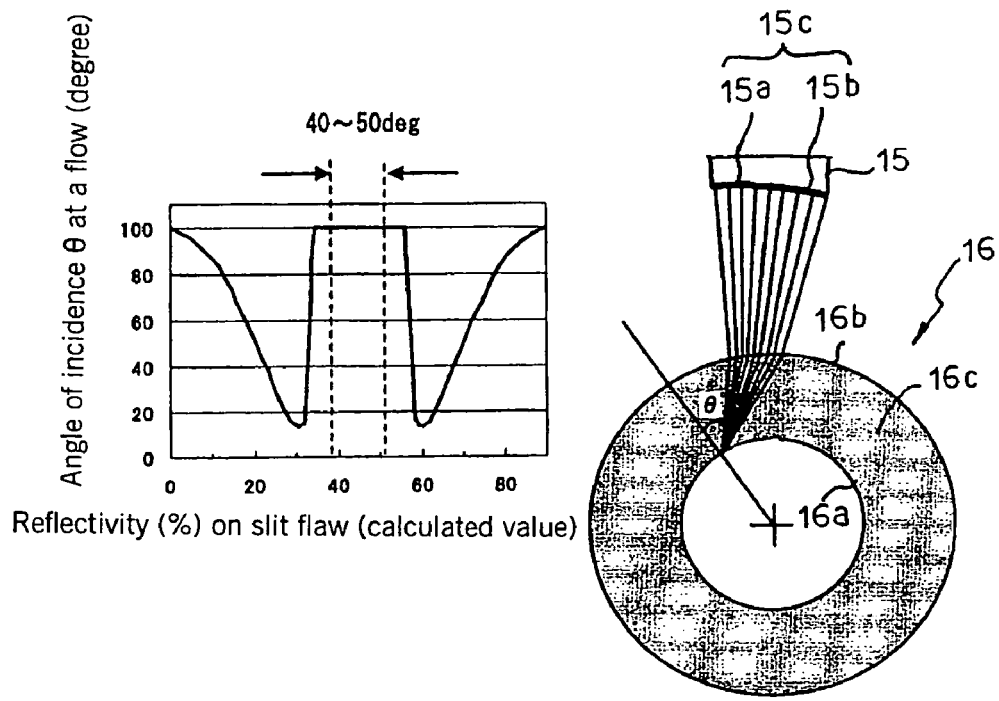
FIG. 6 is a graph showing the relationship between the flaw angle of incidence θ and the reflectivity (%) of a slit flaw present in the form of a slit extending in the axial direction of a high t/D metal pipe.

This provisional setting of the focal point 17 preferably takes the reflectivity of flaws into consideration. Namely, as shown in FIG. 6 which explains the relationship between the angle of incidence θ at a flaw and the reflectivity (percent) on a slit flaw present in the shape of a slit extending in the axial direction of the high t/D metal pipe 16, the reflectivity of refracted transverse waves U2 on a slit flaw depends on the angle of incidence θ of transverse ultrasonic waves. If the range of angles of incidence θ which can be actually set is considered, the echo height from the flaw increases when the angle of incidence θ is around 40-50°. In order to increase the accuracy of flaw detection and increase the echo height from a flaw, a focal point 17 for which the angle of incidence θ becomes around 40-50° is preferably provisionally set as an origin. Then, the procedure proceeds to S3.

In S3, based on above-described conditions (1), (2), (4), and (6), the propagation paths of refracted transverse waves U2 propagated to provisionally set focal point S are calculated. Namely, as shown in FIG. 4A, first, a plurality of propagation paths of the refracted transverse waves U2 are drawn radially from the focal point 17 set on the inner surface 16a of the high t/D metal pipe 16 towards the outer surface 16b (in actuality, the refracted transverse waves U2 propagate from the outer surface 16b towards the focal point 17), and then, based on Snell's law at the interface between the outer surface 16b of the high t/D metal pipe 16 and the couplant W, the angle of incidence of the incident waves is calculated based on above-described conditions (2) and (4), and each of the propagation paths of longitudinal ultrasonic waves U in the couplant W connected to each of the propagation paths of the refracted transverse waves U2 is calculated. Then, the origin of each propagation path of the refracted longitudinal waves U1 and the refracted transverse waves U2 propagating to the focal point 17, i.e., the end point 18 at the opposite side from the focal point 17 is set so that the origin 18 is spaced from the high t/D metal pipe 16 by just a distance roughly equal to the estimated offset distance between the transducer 15 and the high t/D metal pipe 16 and so that the propagation time of the ultrasonic waves along each of the propagation paths (calculated by the lengths of the propagation paths and the velocity of waves) are the same as each other.

In this manner, in S1-S3, the propagation paths of the refracted transverse waves U2 which propagate to the focal point 17 are calculated from Snell's law based on the shape (the outer diameter D, the wall thickness t, and the like) of the high t/D metal pipe 16 undergoing flaw detection, the sound velocity V2 of refracted transverse waves U2 in the metal pipe 16, the sound velocity Vi of incident waves in the couplant, and the focal point 17 of refracted transverse waves U2 in the metal pipe 16. Then, the procedure proceeds to S4.

In S4, based on the propagation paths calculated in S3 and above-described condition (5) (the length of the transducer 15 in the circumferential direction of the high t/D metal pipe 16), the shape of the front end portion 15c of the transducer 15 is calculated. Namely, the length of a curve successively connecting the origins 18 of each of the propagation paths or a curve estimated by the least squares method based on the origins 18 is calculated. This is compared with above-described condition (5), and unneeded propagation paths are deleted from the ends so that both have roughly the same length, and the curve D found from the origins 18 of the remaining propagation paths is made the longitudinal cross-sectional shape of the front end portion 15c of the transducer 15. The example shown in FIG. 4A shows the case in which unneeded propagation paths are deleted so as to achieve a shape of the front end portion such that the lengths of the front end portion on the left and right sides are roughly the same with respect to the central axis of the high t/D metal pipe 16.

In this manner, in S4, based on the propagation paths calculated in S3 and the previously set length in the circumferential direction of the high t/D metal pipe 16 of the transducer 15, the shape of the front end portion 15c of the transducer 15 is calculated and determined so as to achieve an asymmetrically curved shape in which, as described above, the radius of curvature progressively increases from one end 15b towards the other end 15a from a radius of curvature $\rho_1$ to a radius of curvature $\rho_2$. Then, the procedure proceeds to S5.

In S5, based on the shape of the front end portion 15c of the transducer 15 determined in S4 and above-described condition (3), the propagation paths of refracted longitudinal waves U1 which propagate in the interior of the high t/D metal pipe 16 are calculated. Namely, as shown in FIG. 4A, for each incident wave U traveling along each propagation path in the couplant W from each origin 18 constituting the set shape of the front end portion 15c of the transducer 15, based on Snell's law at the interface between the outer surface 16b of the high t/D metal pipe 16 and the couplant W, based on condition (3), the angle of refraction of the longitudinal ultrasonic waves U1 which propagate in the interior 16c of the high t/D metal pipe 16 is calculated, and the propagation paths of the refracted longitudinal waves U1 connecting each of the propagation paths of the incident waves U are calculated.

In this manner, in S5, based on the shape of the front end portion 15c of the transducer 15 calculated in S2 and the previously set sound velocity VL of the refracted longitudinal waves U1 in the metal pipe 16, the propagation paths of the refracted longitudinal waves U1 which propagate inside the metal pipe 16 are calculated based on Snell's law. Then, the procedure proceeds to S6.

In S6, it is determined whether any of the propagation paths of refracted longitudinal waves U1 calculated in S5 reach the inner surface 16a of the high t/D metal pipe 16. The example shown in FIG. 4A is a case in which there are propagation paths which reach the inner surface 16a.

In the case in which there are propagation paths which reach the inner surface 16a, the procedure proceeds to S7, and the provisionally set focal point 17 of the refracted transverse waves U2 is changed to a position spaced along the inner peripheral surface 16a by a prescribed pitch, and then the calculations of above-described S1-S6 are repeated.

Figure 4B:
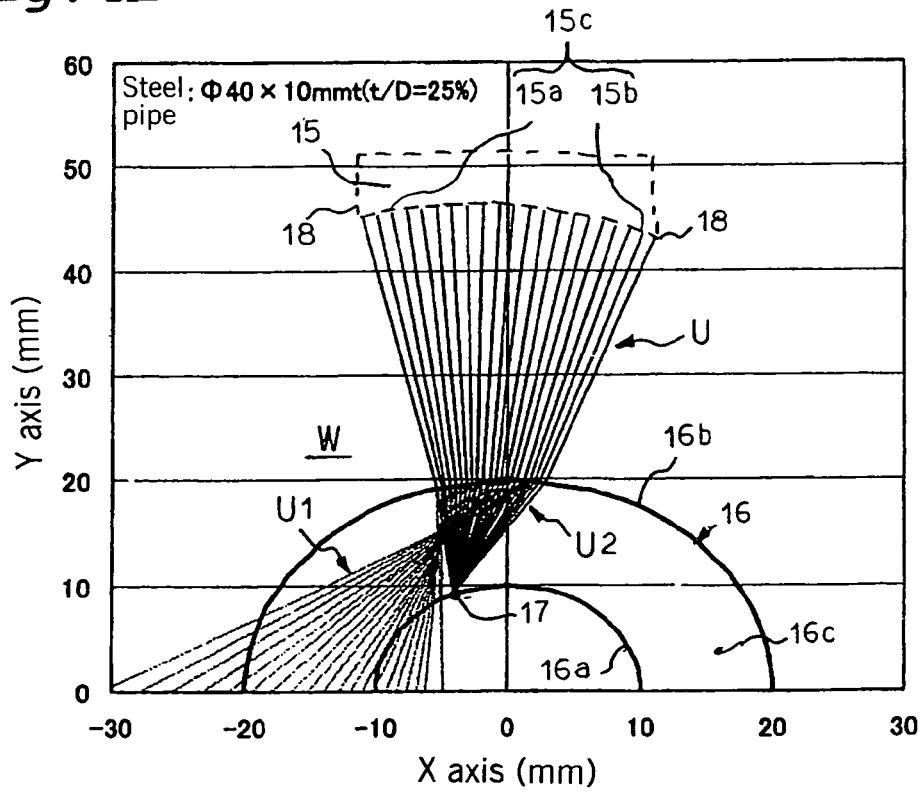
FIG. 4B is an explanatory view showing a step in designing the shape of the front end portion of a transducer when a high t/D metal pipe with an outer diameter of 40 mm and a wall thickness of 10 mm is the object being inspected.
Figure 4C:
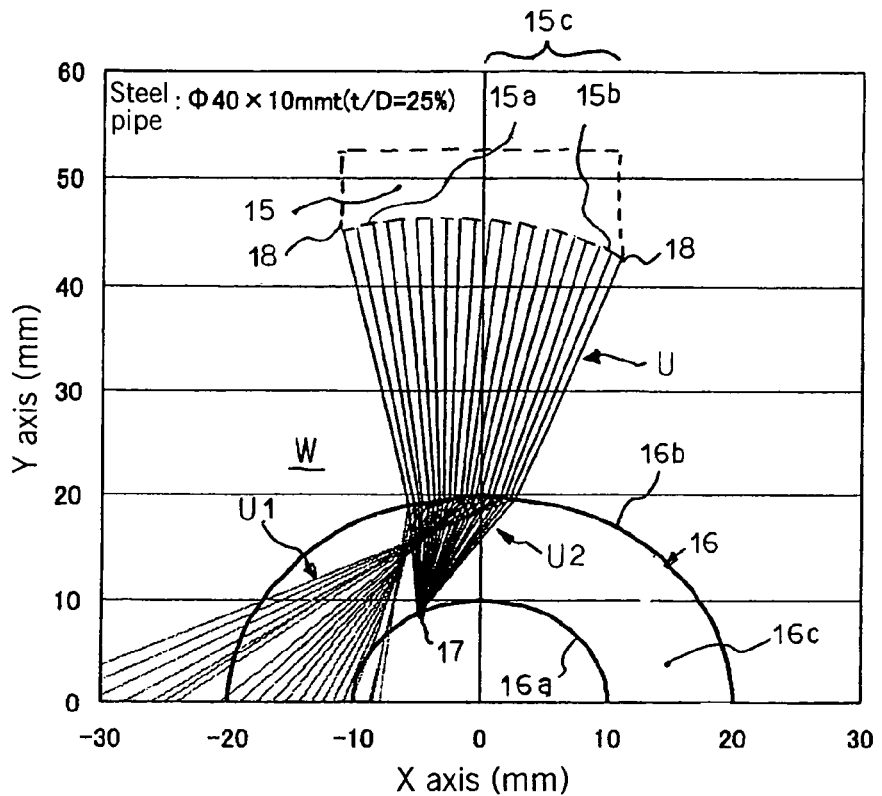
FIG. 4C is an explanatory view showing a step in designing the shape of the front end portion of a transducer when a high t/D metal pipe with an outer diameter of 40 mm and a wall thickness of 10 mm is the object being inspected.
Figure 4D:
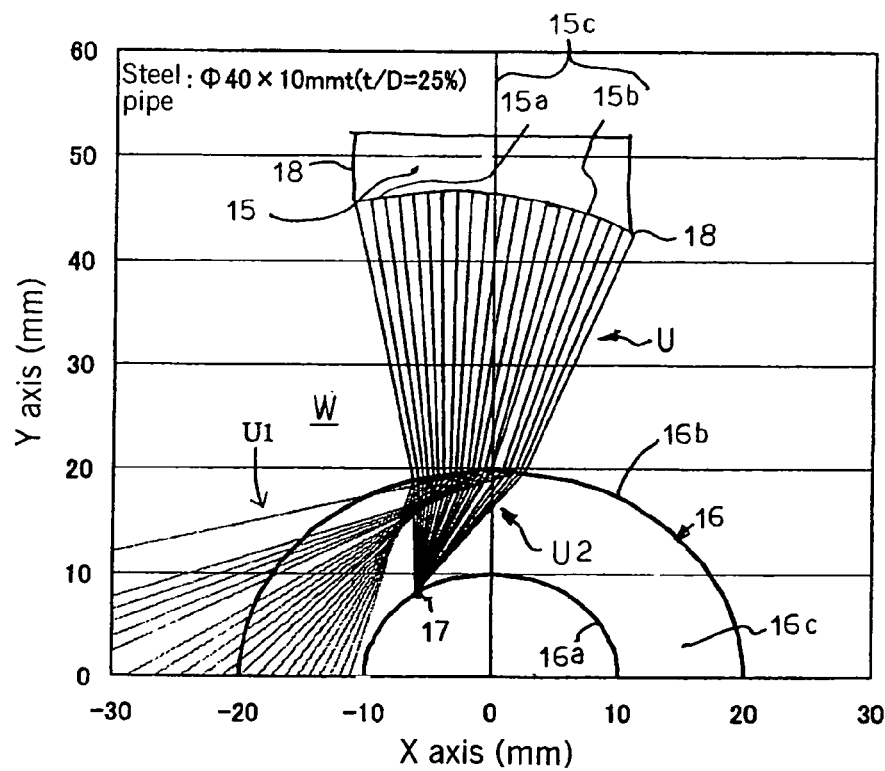
FIG. 4D is an explanatory view showing a step in designing the shape of the front end portion of a transducer when a high t/D metal pipe with an outer diameter of 40 mm and a wall thickness of 10 mm is the object being inspected.

FIGS. 4B-4D are explanatory views showing this repeated calculation. As shown in FIGS. 4B-4D, the set position of the focal point 17 is changed by being spaced in steps from the central axis of the high t/D metal pipe 16 along the inner surface 16a of the high t/D metal pipe 16. As a result, in the state shown in FIG. 4D, none of the propagation paths of the refracted longitudinal waves U1 reaches the inner surface 16a of the high t/D metal pipe 16 any more.

When propagation paths which reach the inner surface P2 no longer exist, the procedure proceeds to S8, and the shape of the front end portion 15c of the transducer 15 which was provisionally set by the immediately preceding calculation is set as the final shape of the front end portion 15c of the transducer 15. In the example shown in FIG. 4A, the shape of the front end portion 15c of the transducer 15 when the state shown in FIG. 4D is achieved is made the final shape of the front end portion 15c.

Thus, in S6-S8, when there exists a propagation path among the propagation paths of the refracted longitudinal waves U1 calculated in S5 which reaches the inner surface 16a of the high t/D metal pipe 16, the focal point 17 of the refracted transverse waves U2 is changed until a propagation path which reaches the inner surface 16a of the high t/D metal pipe 16 no longer exists, the calculations from S1 to S3 are repeated, and when a propagation path which reaches the inner surface 16a of high t/D metal pipe 16 no longer exists, the shape calculated in S2 at that time is set as the shape of the front end portion 15c of the transducer 15.

By the above-described steps S1-8, the front end portion 15c of the transducer 15 is set to have an asymmetrically curved shape having a radius of curvature which progressively increases from one end 15b towards the other end 15a from a radius of curvature $\rho_1$ to a radius of curvature $\rho_2$.

The above explanation is of the case in which the entirety of the front end portion 15c of the transducer 15 is given this asymmetrically curved shape, but the invention is not restricted thereto, and the case in which, for example, a region of the front end portion 15c is given this asymmetrically curved shape and the remaining region of the front end portion 15c is given a shape other than this asymmetrically curved shape (such as a linear shape or an arcuate shape) is also possible. For example, the present invention includes the case in which a portion with an asymmetrically curved shape is present in an intermediate region in the circumferential direction of the front end portion 15c of the transducer 15 and a portion with a shape other than an asymmetrically curved shape exists at one or both sides of the region with an asymmetrically curved shape.

In order to carry out angle beam flaw detection of a high t/D metal pipe 16, as the ratio (t/D) of the high t/D metal pipe increases, the proportion occupied by the portion with an asymmetrically curved shape formed on the front end portion 15c of the transducer 15 with respect to the entire front end portion 15c in the circumferential direction increases. When the ratio (t/D) is around 15%, this proportion is 70%. Therefore, the proportion of the portion or region with an asymmetrically curved shape formed on the front end portion 15c of the transducer 15 with respect to the entire front end portion 15c in the circumferential direction is preferably at least 70% and more preferably at least 80% when the object being inspected is a high t/D metal pipe 16 for which the ratio (t/D) is at least 15%.

The relationship between radius of curvature $\rho_1$ and radius of curvature $\rho_2$ is such that $\rho_1 < \rho_2$. The radius of curvature can be suitably selected based on the relationship between the outer diameter and the wall thickness of the pipe being measured. As a result, angle beam flaw detection can be carried out on a high (t/D) pipe with a specific ratio (t/D) without producing multiple reflection of refracted longitudinal waves.

The above-described Steps S1-8 can be carried out each time by drawing a diagram by a designer, but they can of course be programmed and automatically carried out, and the latter is preferred from the standpoint of design efficiency.

In FIGS. 4A-4D, for ease of explanation, an explanation was given of an example of steps of designing the shape of the front end portion 15c such that the front end portion of each cross section of the transducer 15 in the axial direction of the high t/D metal pipe 16 becomes a uniform curved line in the same manner as a conventional cylindrical surface by analyzing the propagation paths of ultrasonic waves two-dimensionally. However, by analyzing the propagation paths of ultrasonic waves three-dimensionally, it is possible to design the shape of the front end portion 15c so that the front end portion of each cross section of the transducer 15 in the axial direction of the high t/D metal pipe has a uniform curved surface.

Figure 5:
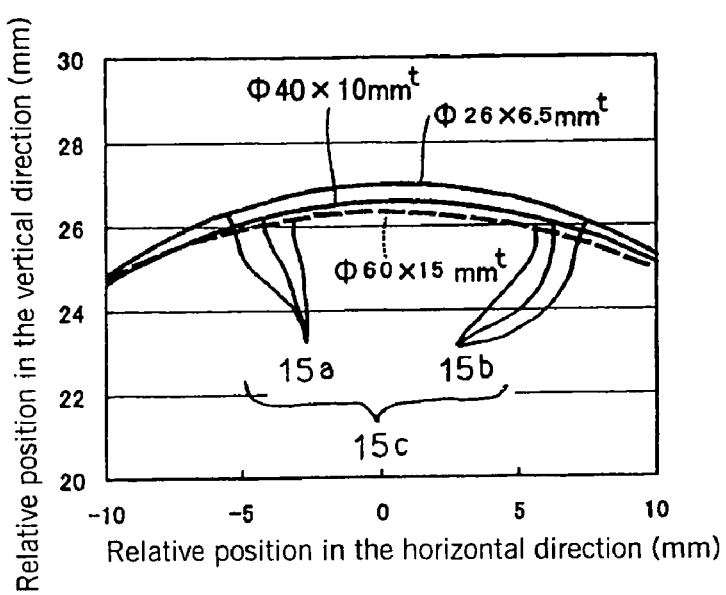
FIG. 5 is an explanatory view showing one example of the results of designing the shape of the front end portion of a transducer based on Steps S1-S8 shown in FIG. 3 for high t/D metal pipes having three different dimensions (an outer diameter of 40 mm and a wall thickness of 10 mm, an outer diameter of 26 mm and a wall thickness of 6.5 mm, and an outer diameter of 60 mm and a wall thickness of 15 mm).

FIG. 5 is an explanatory view showing one example of the result of design of the shape of the front end portion 15c of a transducer 15 based on the above-described steps S1-8 for high t/D metal pipes 16 having three different dimensions (an outer diameter of 40 mm and a wall thickness of 10 mm, an outer diameter of 26 mm and a wall thickness of 6.5 mm, and an outer diameter of 60 mm and a wall thickness of 15 mm). In FIG. 5, in order to make the differences in the shapes of the front end portions 15c of the transducers 15 designed in accordance with each of the dimensions of the high t/D metal pipes 16 clear, the shapes of the designed front end portions 15c are shown together with their positions moved in parallel in the horizontal direction (X-axis) and vertical direction (Y-axis).

As shown in FIG. 5, the shapes of these front end portions 15c are asymmetrically curved shapes for which the radius of curvature progressively increases from a radius of curvature $\rho_1$ to a radius of curvature $\rho_2$ from one end 15b towards the other end 15a.

As shown in FIG. 5, this embodiment is not limited to being applied to a high t/D metal pipe having an outer diameter of 40 mm and a wall thickness of 10 mm which was explained while referring to FIGS. 4A-4D, and it can be applied in the same manner to a metal pipe with a usual ratio (t/D) or to high t/D metal pipes with various dimensions.

The above-described ultrasonic probe 11 is constructed so as to transmit incident waves U directly from the transducer 15, but instead, an acoustic lens (not shown) made of, for example, an acrylic resin or the like may be disposed in front of the transducer 15 in the direction of generation of ultrasonic waves, and incident waves U can be obliquely incident on a high t/D metal pipe 16 through the acoustic lens to generate refracted longitudinal waves U1 and refracted transverse waves U2 which propagate inside the high t/D metal pipe 16. In this case, the transducer 15 may have a front end portion with a usual circular-arc shape, and the front end portion of the acoustic lens may be given an asymmetrically curved shape having a radius of curvature which increases continuously from one end towards the other end from a radius of curvature $\rho_1$ to a radius of curvature $\rho_2$. By doing so, it is possible to use a ceramic piezoelectric element typified by PZT having poor workability but having a good piezoelectric effect as a transducer 15.

An ultrasonic probe 11 of this embodiment is constituted as described above.

[Ultrasonic Flaw Detector 12]

As shown in FIG. 2, an ultrasonic flaw detector 2 according to this embodiment has a pulser 19, a preamplifier 20, a filter 21, a main amplifier 22, and a flaw determining part 23.

The pulser 19 and the preamplifier 20 are both connected to the transducer 15 through a connecting plug provided in the rear portion of a casing of the ultrasonic flaw detector 11 by coaxial cables C (both not shown). A transmitted signal is input from the pulser 19 to the transducer 15 at prescribed intervals, the transducer 15 is thereby excited, and incident waves U are incident on the high t/D metal pipe 16 through water W as a couplant. Then, the incident waves U are propagated inside the high t/D metal pipe 16 as refracted waves comprising refracted longitudinal waves U1 and refracted transverse waves U2. Their reflected echoes (flaw echoes and the like) are received by the transducer 15, and the received signal is transmitted to the preamplifier 20 through the coaxial cables C. The received signal is amplified by the preamplifier 20, and after filtering in a prescribed frequency band is performed by the filter 21, the signal is further amplified by the main amplifier 22. The output signal from the main amplifier 22 is compared with a previously set prescribed threshold value in a flaw determining part 23. The flaw determining part 23 determines that there is a flaw if the output signal is larger than the threshold value, and when it is determined that there is a flaw, an operating command is output to the alarm 3 and the marking device 4.

The ultrasonic flaw detector 12 of this embodiment is a well-known ordinary one constituted as described above, so a further explanation of the ultrasonic flaw detector 12 will be omitted.

[Alarm 13]

The alarm 13 outputs an alarm sound in response to an operating command from the ultrasonic flaw detector 12.

The alarm 13 of this embodiment is a well-known ordinary one having the structure described above, so a further explanation of the alarm 13 will be omitted.

[Marking Device 14]

The marking device 14 carries out prescribed marking of the surface of the high t/D metal pipe 16 in response to an operating command from the ultrasonic flaw detector 12.

The marking device 14 of this embodiment is a well-known ordinary one have a structure as described above, so a further explanation of the marking device 14 will be omitted.

Flaw detection of a high t/D metal pipe 16 using this embodiment of an ultrasonic flaw detection apparatus 10 having this structure will be explained.

In this embodiment, as shown in FIG. 2, the transducer 15 is positioned with respect to the high t/D metal pipe 16 so that as viewed from the center of the high t/D metal pipe 16 which is the object of ultrasonic flaw detection, one end 15$b$ of the front end portion 15$c$ of the transducer 15 of the ultrasonic probe 11 which constitutes an ultrasonic flaw detection apparatus 10 of this embodiment is positioned on the side away from the direction of propagation of refracted waves in the high t/D metal pipe 16 (on the right side of the high t/D metal pipe 16 of FIG. 2), and the other end 15$a$ of the front end portion 15$c$ of the transducer 15 is positioned on the side in the direction of propagation of refracted waves (on the left side in FIG. 1 ($a$)), and angle beam flaw detection is carried out.

Namely, the ultrasonic probe 11 is positioned with respect to the high t/D metal pipe 16 so that one end 15$b$ of the front end portion 15$c$ of the transducer 15 is positioned on the side away from the direction of propagation of refracted waves in the high t/D metal pipe 16 (on the right side of the high t/D metal pipe 16 of FIG. 2), and the other end 15$a$ of the front end portion 15$c$ of the transducer 15 is positioned on the side in the direction of propagation of refracted waves (on the left side of the t/D metal pipe 16 of FIG. 2).

If the ultrasonic probe 11 is positioned with respect to the high t/D metal pipe 16 in this manner, the angle of incidence of incident waves U transmitted from the other end 15$a$ having a larger radius of curvature and the angle of refraction of the refracted longitudinal waves U1 can be made large values.

Accordingly, according to this embodiment, of refracted waves 2 and 3 which are propagated inside the high t/D metal pipe 16 having a ratio (t/D) of at least 15%, the refracted transverse waves U2 can be focused and the refracted longitudinal waves U1 can be prevented from reaching the inner surface 16$a$ of the metal pipe 16.

By focusing the refracted transverse waves U2, the strength of reflected echoes from minute flaws is increased, and refracted longitudinal waves U1 follow a propagation path which does not reach the inner surface 16$a$ of the metal pipe 16, so the occurrence of multiply reflected echoes by the refracted longitudinal waves can be eliminated. As a result, high accuracy angle beam flaw detection can be carried out with certainty, particularly with respect to a high t/D metal pipe 16.

Therefore, according to this embodiment, minute flaws present inside a high t/D metal pipe 16 such as one having a ratio (t/D) of at least 15% can undergo flaw detection with high accuracy and certainty by angle beam flaw detection without an accompanying decrease in inspection inefficiency or increase in inspection costs.

When performing flaw detection of a high t/D metal pipe 16 using an ultrasonic flaw detection apparatus 10 having the structure explained above, the high t/D metal pipe 16 is transported in the axial direction while rotating in the circumferential direction, whereby it is possible to perform flaw detection over roughly the entire surface of the high t/D metal pipe 16. However, the invention is not limited thereto, and the ultrasonic probe 10 may be rotated in the circumferential direction of the high t/D metal pipe 16 while the high t/D metal pipe 16 is transported straight ahead in its axial direction.

An ultrasonic flaw detection apparatus 10 according to this embodiment is particularly suitable for flaw detection of the interior of a steel pipe having a ratio (t/D) of at least 15% such as mechanical tubing used in automotive parts and the like or stainless steel pipe and the like used in high temperature environments.

Figure 7:
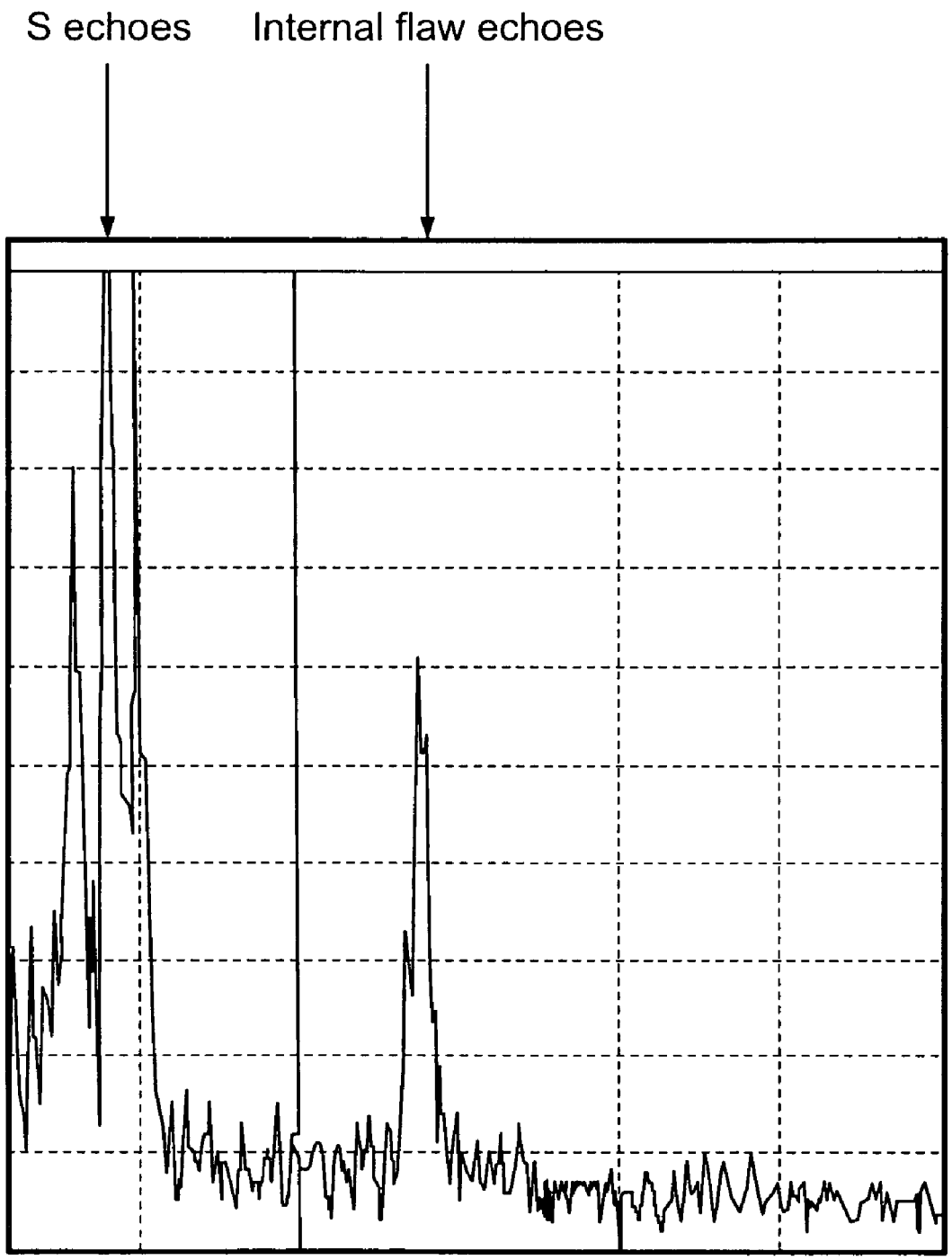
FIG. 7 is a graph showing one example of the flaw detection waveform which is the waveform of the output signal of the main amplifier obtained when performing flaw detection of a minute flaw with a depth of 0.1 mm present in the inner surface of a mechanical tube comprising a high t/D metal pipe by a first embodiment of an ultrasonic flaw detection apparatus.

FIG. 7 is a graph showing an example of a flaw detection waveform which is the output signal waveform of the main amplifier 24 which was obtained when performing flaw detection of a minute flaw with a depth of 0.1 mm present on the inner surface of a mechanical tube comprising a high t/D metal pipe by the ultrasonic flaw detection apparatus 10 according to this embodiment.

As shown in the graph of FIG. 7, with an ultrasonic flaw detection apparatus 10 according to this embodiment, of refracted waves U1 and U2, refracted transverse waves U2 are focused on the interior of the high t/D metal pipe 16, whereby the strength of reflected echoes from minute flaws is increased, while the refracted longitudinal waves U1 which are simultaneously generated follow a propagation path which does not reach the inner surface 16a of the high t/D metal pipe 16, so multiply reflected echoes due to the refracted longitudinal waves U1 can be suppressed, and it is possible to detect only the flaw echoes with a good S/N ratio.

Second Embodiment

Figure 8:
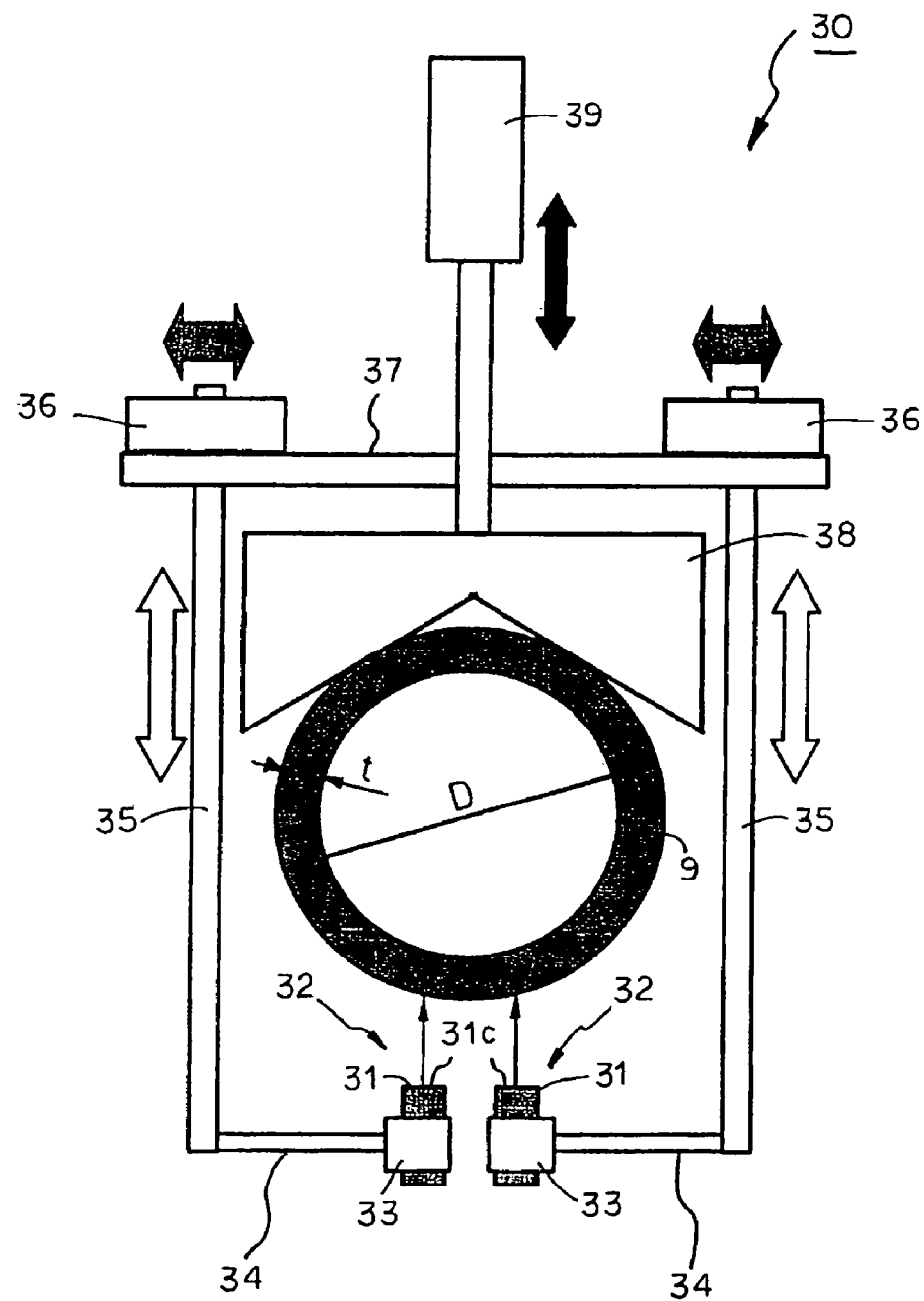
FIG. 8 is an explanatory view schematically showing the structure of a second embodiment of an ultrasonic flaw detection apparatus.

FIG. 8 is an explanatory view schematically showing the structure of an ultrasonic flaw detection apparatus 30 of this embodiment.

As shown in FIG. 8, an ultrasonic flaw detection apparatus 30 according to this embodiment has two ultrasonic probes 32 each having a transducer 31, 31, an ultrasonic flaw detector (not shown), an alarm (not shown), and a marking device (not shown). The unillustrated ultrasonic flaw detector, alarm, and marking device have the same structure as in the above-described first embodiment, so an explanation thereof will be omitted.

This ultrasonic flaw detection apparatus 30 has probe holders 33, 33 which respectively hold transducers 31, 31, lower horizontal arms 34, 34 which respectively hold probe holders 33, 33, vertically movable arms 35, 35 which support the lower horizontal arms 34, 34 and are connected in the vertical direction with an upper horizontal arm 37, horizontally movable arms 36, 36 which are secured to the upper portion of the vertically movable arms 35, 35 and are installed so as to be able to move the upper surface of the upper horizontal arm 37 in the direction in which the upper horizontal arm 37 extends (to the left and right in FIG. 8), the upper horizontal arm 37 which is mounted so as to be able to move the horizontally movable arms 36, 36 and the vertically movable arms 35, 35 in the horizontal direction and which is supported so as to be raised and lowered by an air cylinder 39, a pipe following mechanism 38 which is supported by the air cylinder 39 so as to be capable of being raised and lowered, and the air cylinder 39.

The probe holders 33, 33 are connected to the pipe following mechanism 38 through the lower horizontal arms 34, 34, the vertically movable arms 35, 35, the horizontally movable arms 36 and 36, and the upper horizontal arm 37. The pipe following mechanism 38 is connected to the air cylinder 37 and moves up and down therewith. When the pipe following mechanism 38 moves up and down, the lower horizontal arms 34, 34, the vertically movable arms 35, 35, the horizontally movable arms 36, 36, and the upper horizontal arm 37 also move up and down, and the probe holders 33, 33 are thereby moved up and down as a unit.

The transducers 31, 31 which constitute the ultrasonic probes 32, 32 have a front end portion which, as shown in FIG. 1, is formed with an asymmetrically curved shape having a radius of curvature which progressively increases from one end 15b towards the other end 15a from a radius of curvature $\rho_1$ to a radius of curvature $\rho_2$ in accordance with the material properties (the sound velocity of refracted longitudinal waves and refracted transverse waves of ultrasonic waves), the outer diameter D, the wall thickness t, and the like of a metal pipe 9 which is being subjected to measurement, and they are mounted manually or automatically in the probe holders 33, 33.

The transducers 31, 31 are disposed so that when the vertically movable arms 35 and the horizontally movable arms 36 are driven, one end 15b of each transducer 31, 31 is positioned with respect to the metal pipe 9 on the side opposite from the direction of propagation of refracted waves in the metal pipe 9 (in FIG. 8, on the righthand portion of the metal pipe 9 for the lefthand transducer 31 and on the lefthand portion thereof for the righthand transducer 31), and the other end 15a is positioned on the side in the direction of propagation of refracted waves (in FIG. 8, on the lefthand portion of the metal pipe 9 for the lefthand transducer 31 and on the righthand portion thereof for the righthand transducer 31).

If the relative positional relationship between the transducers 31, 31 and the metal pipe 9 deviates, the location of the focal point (symbol 17 in FIG. 2) of the transverse ultrasonic waves in the metal pipe 9 which was assumed when determining the asymmetrically curved shape of the front end portions 31c, 31c of the transducers 31, 31 deviates, so the ability to detect flaws decreases. Accordingly, in order to accurately set the relative positional relationship between the transducers 31, 31 and the metal pipe 9, linear guides are preferably used as the vertically movable arms 35, 35 and the horizontally movable arms 36, 36.

When performing flaw detection of a metal pipe 9 using an ultrasonic flaw detection apparatus 30 having the above-described structure, in a state in which the front end portions of the metal pipe 9 are sealed by plugs (not shown) for preventing ingress of water, the metal pipe 9 is passed through a flaw detection water tank (not shown) by being transported in its axial direction while rotating in the circumferential direction.

At this time, the air cylinder 37 is started when the front end portion of the metal pipe 9 is sensed by a prescribed material sensing sensor, the pipe following mechanism 38, the vertically movable arms 35, 35, the horizontally movable arms 37, and the probe holders 36, 36 are lowered by it as a single unit, and the pipe following mechanism 38 is pressed against the outer surface of the metal pipe 38 with a suitable pressure.

The pipe following mechanism 38 which is pressed with a suitable force is constituted so as to be able to move up and down and side to side within just a prescribed range, so it follows vibrations during transport of the metal pipe 9 and moves up and down and side to side while maintaining a state in which its lower surface contacts the outer surface of the metal pipe 9. At this time, the vertically movable arms 35, 35, the horizontally movable arms 36, 36, and the probe holders 38 connected to the following mechanism 38 also perform following by moving up and down and side to side. As a result, the positional relationship between the transducers 31, 32 mounted on the probe holders 33, 33 and the metal pipe 9 is maintained constant.

In this manner, with the ultrasonic flaw detection apparatus 30 of this embodiment as well, the strength of reflected echoes from minute flaws is increased by focusing refracted transverse waves, and refracted longitudinal waves which are generated at the same time follow a propagation path which does not reach the inner surface of the metal pipe 9, so the occurrence of multiply reflected echoes by refracted longitudinal waves can be eliminated, and it is possible to detect just flaw echoes with a good S/N ratio.

In the ultrasonic flaw detection apparatus 30 shown in FIG. 8, an example was given of a form in which two transducers 31, 31 are installed so that the directions of propagation of refracted waves in the metal pipe 9 are in the clockwise direction as well as in the counterclockwise direction, but in order to further increase flaw detection efficiency, it is possible that a plurality of transducers 31 having clockwise direction of propagation of refracted waves and those having counterclockwise direction of propagation of refracted waves are installed in the axial direction of the metal pipe 9.

Third Embodiment

In this third embodiment, in contrast to the above-described first and second embodiments, the case will be explained in which the transducer is constituted by a plurality of oscillation-generating elements disposed side by side so as to have a planar shape.

Figure 9:
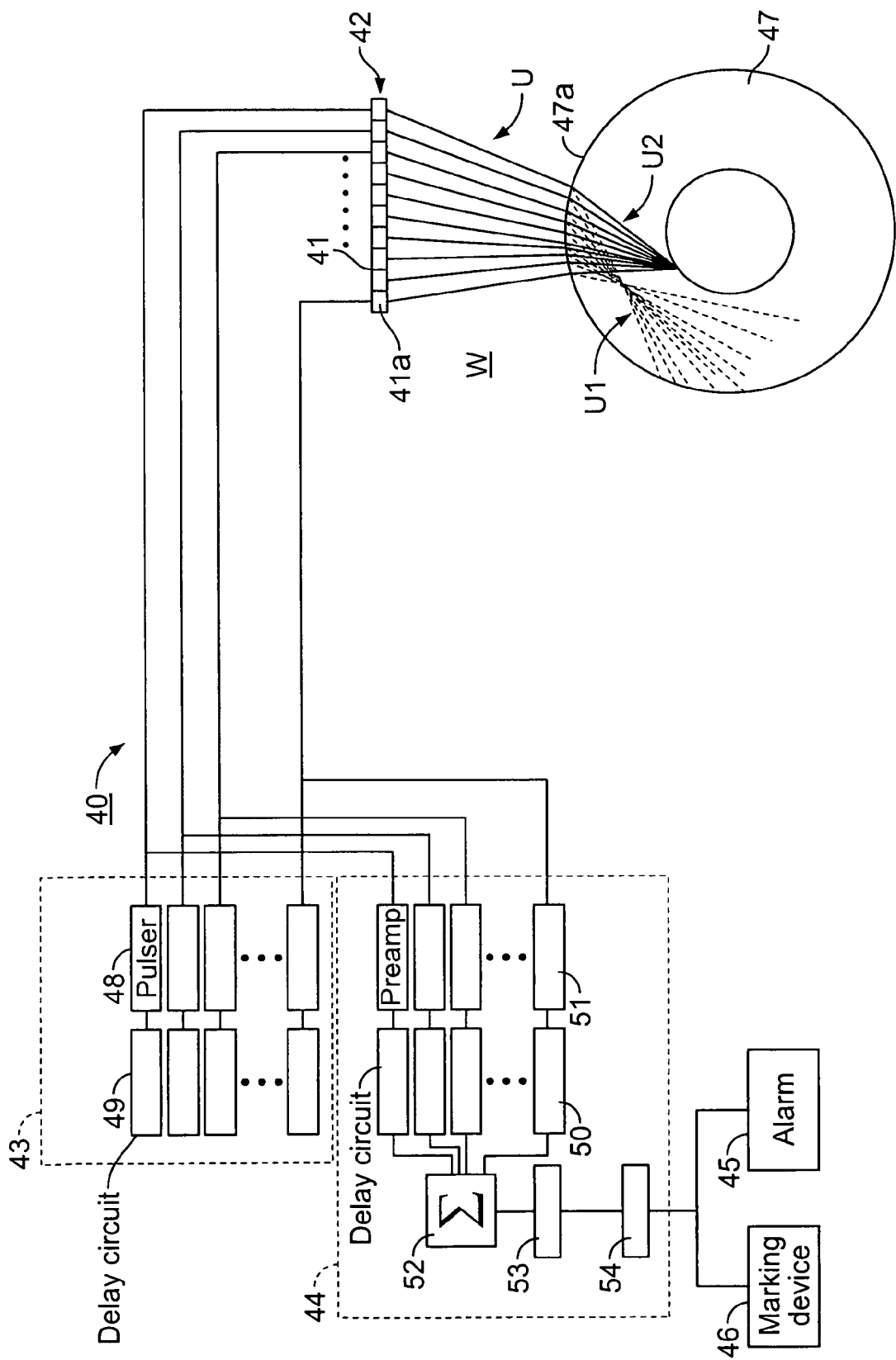
FIG. 9 is a block diagram schematically showing the structure of a third embodiment of an ultrasonic flaw detection apparatus.

FIG. 9 is a block diagram schematically showing the structure of an ultrasonic flaw detection apparatus 40 according to this embodiment. As shown in this figure, the ultrasonic flaw detection apparatus 40 according to this embodiment has an ultrasonic probe 42 equipped with a transducer 41, a transmission circuit 43, a receiving circuit 44, an alarm 45, and a marking device 46. The alarm 45 and the marking device 46 have the same structure as in the above-described first embodiment, so an explanation thereof will be omitted.

The transducer 41 constituting the ultrasonic probe 42 according to this embodiment is constituted by a plurality (such as 32) of minute piezoelectric elements 41a which oppose the outer surface 47a of a metal pipe 47 and are arranged side by side in a straight line in a direction perpendicular to the axial direction of the metal pipe 47 with a spacing of 0.5 mm, for example. The ultrasonic probe 42 is thus a so-called array probe.

The transmitting circuit 43 is equipped with the same number of pulsers 48 and delay circuits 49 (transmission delay circuits) as the number of piezoelectric elements 41a in the probe 41. Each pulser 48 is connected to one of the piezoelectric elements 41a of the probe 41 and to one of the delay circuits 49. Each piezoelectric element 41a is excited at prescribed intervals by a transmitted signal from the pulser 48 connected to the piezoelectric element 41a, and it produces incident ultrasonic waves U which are incident on the metal pipe 47 through water W as a couplant.

The timing of transmission of the transmission signals from each of the pulsers 48 can be made different for each pulser 48 in accordance with a transmission delay time set by each delay circuit 49. By suitably setting the transmission delay time for each pulser 48 in the manner described below, a mode can be realized which is the same as the mode shown in the first and second embodiment in which incident ultrasonic waves U are transmitted from a transducer having a front end portion with an asymmetrically arc curved shape.

The incident waves U which are incident on the metal pipe 47 are propagated to the interior 47c of the metal pipe 47 as refracted waves comprising refracted longitudinal waves U1 and refracted transverse waves U2, their reflected echoes are received by the piezoelectric elements 41a of the transducer 41, and the received signals are sent to the receiving circuit 44.

The receiving circuit 44 is equipped with the same number of preamplifiers 50 and delay circuits 51 (receiving delay circuits) as the number of piezoelectric elements 41a with which the transducer 41 is equipped. The receiving circuit 44 has an adder 52, a main amplifier 53, and a flaw determining part 54. Each preamplifier 50 is connected to one of the piezoelectric elements 41a of the transducer 41 and to one of the delay circuits 51. The received signal from each piezoelectric element 41a is amplified by one of the preamplifiers 50 connected to the piezoelectric element 41a, and then it is delayed by the delay circuit 51 connected to the preamplifier 50 by the same receiving delay time as the transmission delay time of the piezoelectric element 41a (the transmission delay time of the pulser 48 connected to the piezoelectric element 41a). The output signals of each of the delay circuits 51 are summed by the adder 52 with which the receiving circuit 44 is equipped, and then the result is amplified by the main amplifier 53. The output signal from the main amplifier 53 is input to a flaw determining part 54 having a structure like that of the flaw determining part 23 of the first embodiment, and it is determined whether there are flaws.

Below, a method of setting the above-mentioned transmission delay time and receiving delay time will be explained.

Figure 10:
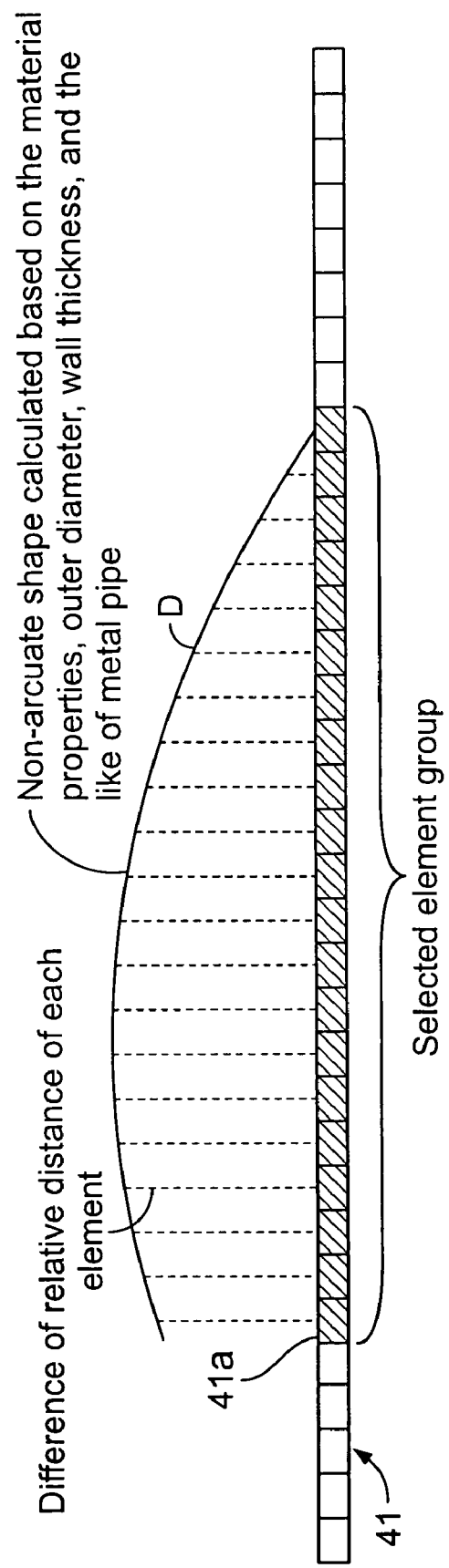
FIG. 10 is an explanatory view for explaining a method of setting the transmission delay time and the reception delay time.
Figure 11:
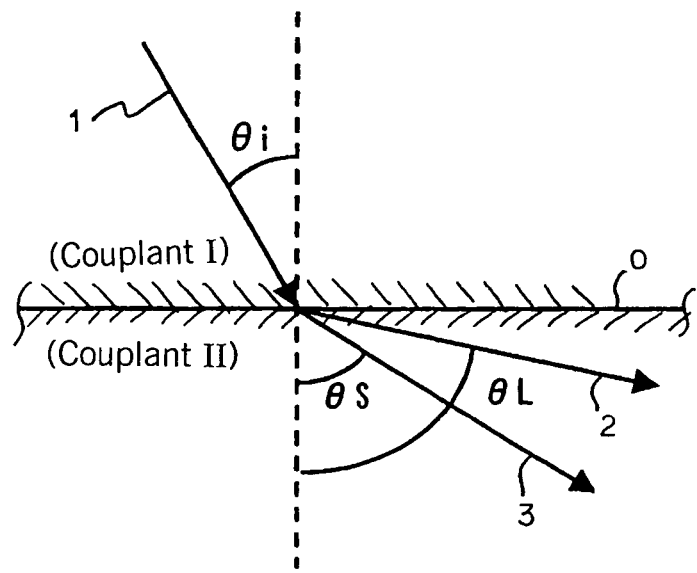
FIG. 11 is an explanatory view showing the relationship between incident waves and refracted waves in an angle beam flaw detection method.
Figure 12:
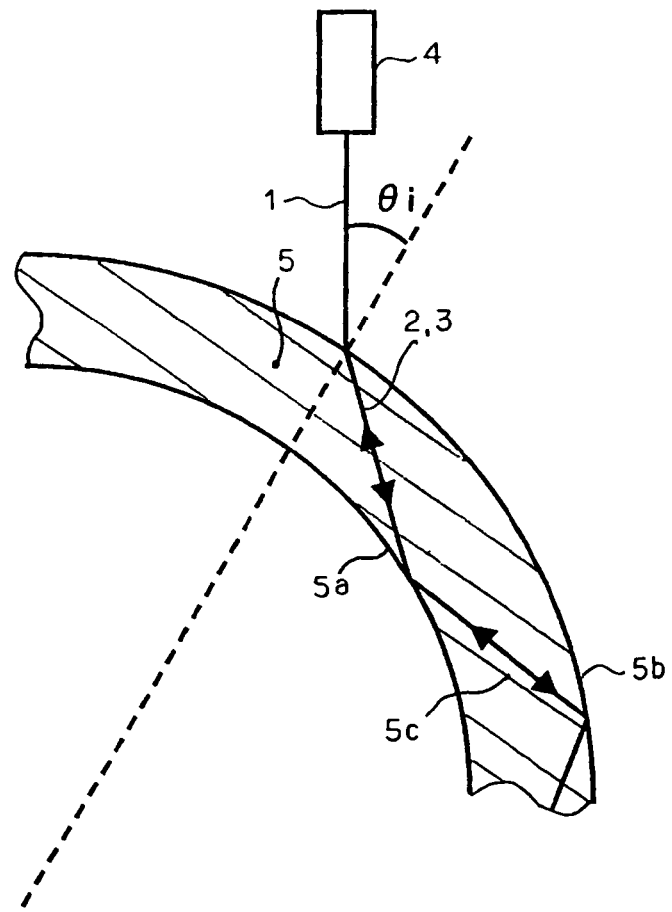
FIG. 12 is an explanatory view showing the propagation of refracted waves inside a metal pipe.
Figure 13:
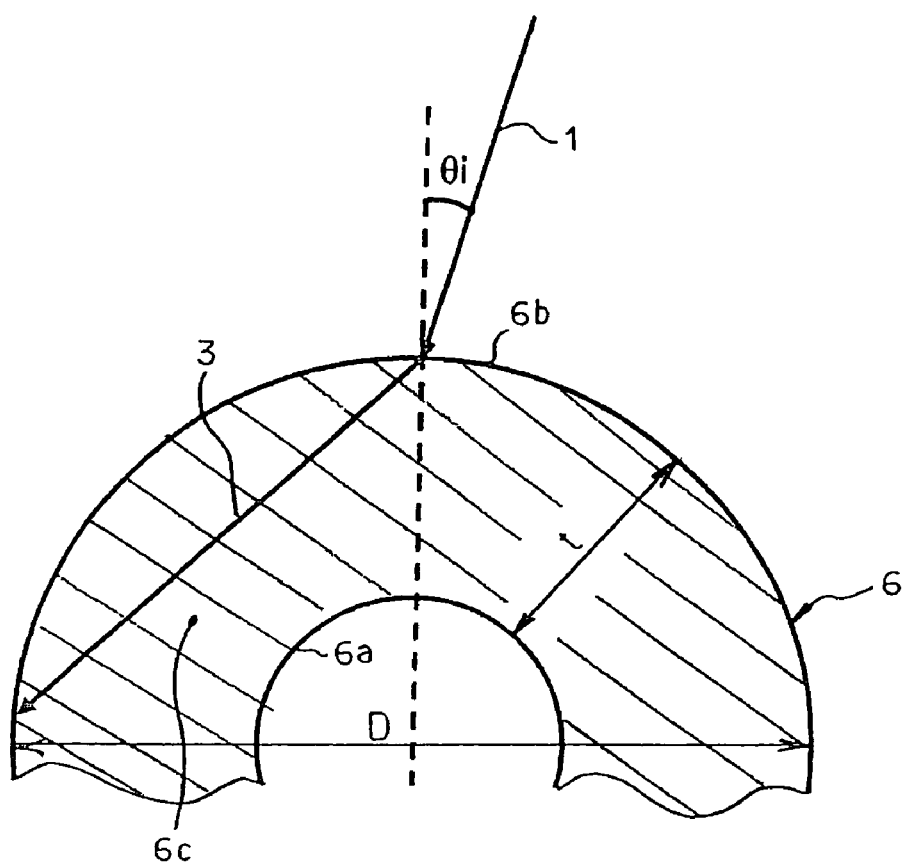
FIG. 13 is an explanatory view showing flaw detection in a high t/D metal pipe by the angle beam flaw detection method.
Figure 15:
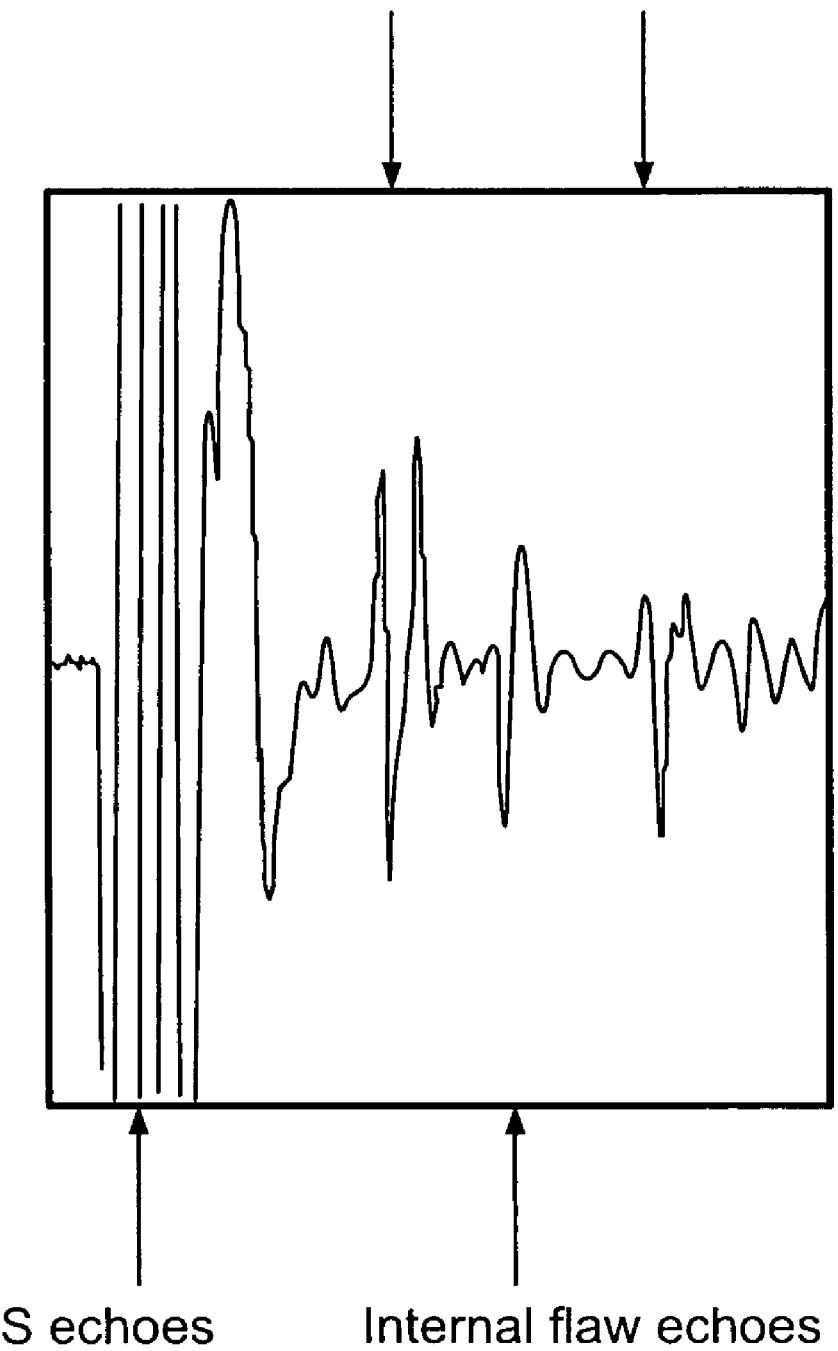
FIG. 15 is a graph showing an example of reflected echoes observed during flaw detection of a high t/D metal pipe.

FIG. 10 is an explanatory view for explaining a method of setting the transmission delay time and the receiving delay time. As shown in this figure, when setting the transmission delay time and the receiving delay time, first, the length in the horizontal direction (to the left and right in FIG. 10) of the asymmetrically curved shape D designed by steps like steps S1-8 shown in FIG. 3 is compared with the length of the transducer 11, and the piezoelectric elements 41a to be used are selected so that both have approximately the same length. The collection of selected piezoelectric elements 41a is referred to as the selected element group.

Next, the coordinates of the center of the piezoelectric elements 41a constituting the selected element group and the relative distance from the asymmetrically curved shape D are calculated, with taking the relative distance between one of the piezoelectric elements 41a and the asymmetrically arcuate shape D as 0 (zero). In FIG. 10, the relative distance between the righthand piezoelectric element 41a and the asymmetrically arcuate shape D was made 0. Then, a value equal to the relative distance divided by the sound velocity of incident waves U in the couplant W is set as the transmission delay time and the receiving delay time corresponding to each element 41a.

With the method described above, by setting the transmission delay time and the reception delay time, the same behavior is exhibited as when ultrasonic waves are transmitted and received using a transducer 41 having a cross sectional end shape which is an asymmetrically curved shape D. Namely, as shown in FIG. 9, of refracted waves comprising refracted longitudinal waves U1 and refracted transverse waves U2 which are propagated on the interior 47c of the metal pipe 47, refracted transverse waves U2 are focused while refracted longitudinal waves U1 do not reach the inner surface 47a of the metal pipe 47. Accordingly, by focusing the refracted transverse waves U2, the strength of reflected echoes from minute flaws is increased, and the occurrence of multiply reflected echoes due to the refracted longitudinal waves U1 which are generated at the same time are eliminated, so it is possible to sense only flaw echoes with a good S/N ratio.

An ultrasonic flaw detection apparatus 40 according to this embodiment has an ultrasonic probe 42 having a transducer 41 constituted by a large number of piezoelectric elements 41a to form an array probe, and the delay times of transmitted and received ultrasonic waves are suitably set for each piezoelectric element 41a, whereby an ultrasonic probe having a transducer having a front end portion with an asymmetrically curved shape as explained with respect to the first and second embodiments is simulated.

Namely, as a result of interference between ultrasonic waves generated by the plurality of oscillation-generating elements, it is possible to have a structure such that incident waves can be generated having a wave front having at least a portion with an asymmetrically curved shape which has a radius of curvature which progressively increases from one end to the other end. As a result, using a transducer 41 having an array of piezoelectric elements 41a which are secured in a straight line as in this embodiment, by simply suitable changing the delay time of the transmission and reception of ultrasonic waves, a transducer providing the same effects as many types of transducers having a front end portion with an asymmetrically curved shape can be provided.

Accordingly, it is not necessary to prepare a large number of transducers with an asymmetrically curved shape in accordance with the material properties, the outer diameter D, the wall thickness t, and the like of a metal pipe 47, and an increase in running costs can be suppressed. In addition, it is not necessary to replace a transducer having an asymmetrically curved shape in accordance with the material properties, the outer diameter D, the wall thickness t, and the like of a metal pipe 47, so the time required for replacement and the like can be shortened, and the efficiency of inspection can be increased.

In this embodiment, the case was explained in which an array probe having piezoelectric elements arranged in a straight line is employed as a transducer 41, but the present invention is not limited thereto, and as long as the delay time for transmission and reception of ultrasonic waves is set in accordance with the arrangement, it is also possible to use an array probe arranged in an arcuate shape or a polygonal shape.

The invention claimed is:

1. An ultrasonic probe which performs flaw detection of a tubular body being inspected by obliquely impinging ultrasonic waves on a tubular metal body being inspected from a transducer housed therein and generating refracted longitudinal waves and refracted transverse waves which are propagated inside the tubular body being inspected, wherein the front end portion of the transducer has at least a portion with an asymmetrically curved shape having a radius of curvature which progressively increases from one end towards the other end of the front end portion and wherein the radius of curvature progressively increases in a longitudinal cross section of the transducer perpendicularly to a longitudinal axis of the tubular body being inspected.

2. An ultrasonic probe as set forth in claim 1 wherein the tubular body being inspected is a metal pipe having a ratio of its wall thickness to its outer diameter of greater than 15%.

3. A method of ultrasonic flaw detection characterized in that an ultrasonic probe as set forth in claim 1 is disposed with respect to a tubular metal body being inspected such that, as viewed from the center of the tubular body being inspected, the end having a smaller radius of curvature of the front end portion of a transducer or an acoustic lens constituting the ultrasonic probe is positioned on the side away from the direction of propagation of refracted waves in the tubular body being inspected and the end having a larger radius of curvature of the front end portion is positioned on the side in the direction of propagation of the refracted waves, and such that incident waves are generated which generate refracted longitudinal waves which do not reach the inner surface of the tubular body being inspected and refracted transverse waves which are focused on the inner surface of the tubular body being inspected, and angle beam flaw detection is carried out.

4. An ultrasonic flaw detection method as set forth in claim 3 characterized by performing angle beam flaw detection of a tubular metal body being inspected for which the ratio of its wall thickness to its outer diameter is greater than 15%.

5. An ultrasonic flaw detection apparatus characterized by being equipped with an ultrasonic probe as set forth in claim 1.

6. An ultrasonic probe which has a transducer housed therein and an acoustic lens which is disposed forward of the transducer in the direction of transmission of ultrasonic waves and which performs flaw detection of a tubular metal body being inspected by obliquely impinging ultrasonic waves on the tubular body being inspected through the acoustic lens and generates refracted longitudinal waves and refracted transverse waves which are propagated inside the tubular body being inspected, wherein the front end portion of the acoustic lens has at least a portion with an asymmetrically curved shape having a radius of curvature which progressively increases from one end towards the other end of the front end portion and wherein the radius of curvature progressively increases in a longitudinal cross section of the transducer perpendicularly to a longitudinal axis of the tubular body being inspected.

7. An ultrasonic probe which performs flaw detection of a tubular metal body being inspected by obliquely impinging ultrasonic waves on the tubular body being inspected from a transducer housed therein and generating refracted longitudinal waves and refracted transverse waves which are propagated inside the tubular body being inspected, wherein the transducer is constituted by a plurality of oscillation-generating elements arranged in parallel, and incident waves are generated having a wave front having at least a portion with an asymmetrically curved shape having a radius of curvature which progressively increases from one end towards the other end of the wave front due to interference of ultrasonic waves generated by the plurality of oscillation-generating elements and wherein the radius of curvature progressively increases in a longitudinal cross section of the transducer perpendicularly to a longitudinal axis of the tubular body being inspected.

8. An ultrasonic probe as set forth in claim 7 having a delay time adjusting device for generating the incident waves by adjusting the delay time for transmission and reception of ultrasonic waves by each of the plurality of oscillation-generating elements.

9. An ultrasonic probe as set forth in claim 8 characterized by having an acoustic lens disposed forward of the transducer in the direction of transmission of ultrasonic waves.

10. A method of ultrasonic flaw detection characterized in that an ultrasonic probe as set forth in claim 7 is disposed with respect to a tubular metal body being inspected such that, as viewed from the center of the tubular body being inspected, the end having a smaller radius of curvature of the wave front at the end of incident waves which are generated by a transducer constituting the ultrasonic probe is positioned on the side away from the direction of propagation of refracted waves in the tubular body being inspected and the end of the wave front having a larger radius of curvature is positioned on the side in the direction of propagation of refracted waves, and such that incident waves are generated which generate refracted longitudinal waves which do not reach the inner surface of the tubular body being inspected and refracted transverse waves which are focused on the inner surface of the tubular body being inspected, and angle beam flaw detection is carried out.

* * * * *